(12) United States Patent
Lozano et al.

(10) Patent No.: US 8,470,565 B2
(45) Date of Patent: Jun. 25, 2013

(54) USE OF IONIC LIQUIDS FOR IMPLEMENTING A PROCESS FOR THE PREPARATION OF BIODIESEL

(75) Inventors: Pedro Lozano, Molina de Segura (ES); Teresa De Diego, Molina de Segura (ES); José Luis Iborra, Churra (ES); Michel Vaultier, Chateaugiron (FR)

(73) Assignees: Centre National de la Recherche Scientifique, Paris (FR); Universidad de Murcia, Murcia (ES)

( * ) Notice: Subject to any disclaimer, the term of this patent is extended or adjusted under 35 U.S.C. 154(b) by 0 days.

(21) Appl. No.: 13/130,463

(22) PCT Filed: Nov. 20, 2009

(86) PCT No.: PCT/EP2009/065586
§ 371 (c)(1),
(2), (4) Date: Aug. 1, 2011

(87) PCT Pub. No.: WO2010/057996
PCT Pub. Date: May 27, 2010

(65) Prior Publication Data
US 2011/0294172 A1  Dec. 1, 2011

(30) Foreign Application Priority Data

Nov. 21, 2008 (EP) ..................................... 08291101

(51) Int. Cl.
*C12P 7/62* (2006.01)
(52) U.S. Cl.
USPC .......................................................... 435/135
(58) Field of Classification Search
None
See application file for complete search history.

(56) References Cited

U.S. PATENT DOCUMENTS

| | | | |
|---|---|---|---|
| 5,354,878 A | 10/1994 | Connemann et al. | |
| 6,398,707 B1 | 6/2002 | Wu et al. | |
| 2003/0032826 A1 | 2/2003 | Hanna | |

FOREIGN PATENT DOCUMENTS

| | | |
|---|---|---|
| EP | 1 705 238 A1 | 9/2006 |
| WO | 2006/050589 A1 | 5/2006 |
| WO | 2007/055661 A1 | 5/2007 |

OTHER PUBLICATIONS

Miyawaki et al.: "Lipase-catalyzed butanolysis of triolein in ionic liquid and selective extraction of product using supercritical carbon dioxide", Journal of Bioscience and Bioengineering, Elsevier, Amsterdam, NL, vol. 105, No. 1, Jan. 1, 2008, pp. 61-64, XP022494317, ISSN: 1389-1723, abstract, figures 3, 4, pp. 61, left-hand column, paragraph 3-right-hand column, paragraph 4.

Gamba M. et al.: "Supported ionic liquid enzymatic catalysis for the production of biodiesel", Advanced Synthesis & Catalysis, Wiley-VCH, Weinheim, vol. 350, No. 1, Jan. 4, 2008, pp. 160-164, XP002527762, abstract; figure 2; tables 1, 2, p. 163, col. 1, paragraph 2, 3, p. 163, col. 2, paragraph 4.

Ha et al.: "Lipase-catalyzed biodiesel production from soybean oil in ionic liquids", Enzyme and Microbial Technology, Stoneham, MA, US, vol. 41, No. 4, Jul. 26, 2007, pp. 480-483, XP022146689, ISSN: 0141-0229, abstract; figures 1-3, pp. 480-482, paragraph 1., 2.2, 3.1, 3.2.

Sunitha S. et al.: "Ionic liquids as a reaction medium for lipase-catalyzed methanolysis of sunflower oil", Biotechnology Letters, Kluwer Academic Publishers, DO, vol. 29, No. 12, Jul. 19, 2007, pp. 1881-1885, XP019548711, ISSN: 1573-6776, abstract; figure 1; tables 1, 2, p. 1882, col. 1, paragraph 4-p. 1884, col. 1, paragraph 1.

Guo et al.: "Functional dependency of structures of ionic liquids: Do substituents govern the selectivity of enzymatic glycerolysis", Organic and Biomolecular Chemistry 2006, Royal Society of Chemistry 2006, Royal Society of Chemistry GB, vol. 4, No. 14, 2006, pp. 2772-2776, XP002527763, abstract; figure 1; table 1.

Madeira et al.: "Lipase-catalyzed Reactions in Ionic Liquids", Organic Letter, American Chemical Society, Columbus, OH; US, vol. 2, No. 26, Jan. 1, 2000, pp. 4189-4191, XP000985324, ISSN: 1523-7060, abstract; table 2, p. 4190, col. 1, paragraph 3, p. 4190, col. 2, paragraph 2.

International Search Report, dated Jun. 8, 2010, from corresponding PCT application.

European Search Report, dated May 25, 2009, from corresponding European application.

*Primary Examiner* — Nashaat Nashed
(74) *Attorney, Agent, or Firm* — Young & Thompson

(57) ABSTRACT

The use of a combination of—at least one ionic liquid which is lipophilic, and non miscible with water, and—at least one enzyme, for the implementation of an esterification and/or transesterification process of a substrate with at least one alcohol, the substrate consisting of oils, fats, fatty acids, or a mixture thereof, wherein the ionic liquid, the substrate, and the alcohol form a single homogeneous liquid phase at the temperature at which the esterification and/or transesterification process is performed.

20 Claims, 26 Drawing Sheets

USE OF IONIC LIQUIDS FOR IMPLEMENTING A PROCESS FOR THE PREPARATION OF BIODIESEL

FIELD OF THE INVENTION

The invention relates to the use of ionic liquids for implementing a process for the preparation of biodiesel.

BACKGROUND OF THE INVENTION

Biodiesel is a liquid fuel originating from renewable resources, i.e. biomass, alternative to fossil oil products, containing alkyl esters (mostly methyl and ethyl) of long chain fatty acids. They are obtained by catalytic transesterification of triacylglycerides, present in vegetable oils (i.e. olive, sunflower, etc) and/or animal fats, with a primary aliphatic alcohol (i.e. methanol, ethanol, usually) acting as acyl acceptor.

The industrial production of biodiesel in Europe, USA and Japan is carried out by chemical processes based on transesterification catalyzed by strong bases or such as for example NaOH, or KOH, which are toxic and corrosive by nature (see U.S. Pat. No. 354,878; US Pat. No 2003/0032826). Biodiesel production by this technology shows several problems, such as the difficulty to recover the by-product glycerol, the necessity to eliminate the base catalyst from the reaction medium by washing with water, which produces large amounts of alkaline wastes. Additionally, the initial content of water and free fatty acids in the vegetable oil or fat used as substrate is a serious drawback, because of the decrease in biodiesel yield due to the undesirable by-products (i.e. soap, emulsions, etc) generated, which makes it necessary to use refined vegetable oils.

Over the last years, the advantages of using immobilized enzymes onto solid supports as catalysts to synthesize products with industrial interest have been widely demonstrated. In this way, the enzymatic synthesis of biodiesel by transesterification from vegetable oils has been widely described (see U.S. Pat. No. 6,398,707 B1; Pat. WO 2006/050589 A1; Pat. WO 2007/055661 A1; Pat. EP 1 705 238 A1; Shimada, Y. et al., 1999, J. Am. Oil Chem. Soc., 76, 789-793; Shimada, Y. et al., 2002, J Mol. Catal B: Enzymatic, 17, 133-142; Soumanou M. and Bornscheuer U. T, 2003, Enzyme Microb. Technol., 33, 97-103; Mahabubur M. D. et al., 2006, Biocatal. Biotrans., 24, 257-262; Royon D. et al., 2006, Biores. Technol., 98, 648-653; Al-Zuhair et al., 2006, Biochem. Eng. J., 30, 212-217). Immobilized lipases used are for instance NOVOZYME 435 (lipase B from *Candida antartica*), LIPOZYME TL (lipase from *Thermomyces lanuginose*), LIPOZYME RM (lipase from *Rhizomucor miehei*).

However, the industrial interest for an enzymatic process in a non-aqueous medium will greatly rely on the activity, stability and recycling ability of the biocatalyst which is used and the easy separation of the biodiesel from reaction mixture and glycerol. In this regards, the synthesis of biodiesel by using immobilized lipases shows several disadvantages, which constitutes a handicap towards their exploitation at industrial scale. Firstly, it is necessary to point out the low solubility and/or immiscibility of both triacylglycerides (i.e. vegetable oil and/or animal fats) and primary aliphatic alcohols (i.e. methanol, ethanol, etc.) assayed in the transesterification reaction, resulting in biphasic systems. Secondly, the hydrophilic nature of these alcohols is detrimental to the immobilized lipases when introduced into the reaction mixture, catalyst particles getting impregnated with the alcohol, which seriously limits the accessibility of triacylglycerides into the enzyme microenvironment and induces the enzyme deactivation. The final result is an important loss in enzyme efficiency which limits the turnover frequency of the enzyme and the number of recycling operations. Furthermore, the transesterification reaction catalyzed by the enzyme yields both the fatty acid alkyl esters (biodiesel) and the by-product glycerol which provokes a continuous poisoning of biocatalyst until full deactivation.

Several strategies have been developed to overcome all the constraints mentioned above. However, the most popular strategy to improve the catalytic efficiency of enzymes in the synthesis of biodiesel is the solubilisation of substrates (triacylglycerides and methanol) in organic solvents having medium polarity, such as, tert-butanol, 2-propanol, 2-butanol or tetrahydrofuran, in a ratio higher than 30% v/v with respect to the substrates. These systems lead to a clear increase in the overall price of the process by both the consumption of the solvent and the necessity to purify the biodiesel product by distillation.

The use of volatile organic solvents, as reaction media in enzymatic processes, shows several disadvantages such as, the necessity of recovery, as a consequence of the high price and environment impact. The use of clean and sustainable technologies in the chemical industry, also called Green Chemistry, is one of the main developments for the near future in our society. In this way, ionic liquids (ILs) have recently emerged as new green solvents and/or reaction media for chemical processes, because of their capacity to constitute a clean alternative, non-pollutant and reusable as compared to volatile organic solvents (VOS).

The use of ILs as reaction media in enzymatic transformations is very recent: the first reference has been published in 2000 (see Erbeldinger, M. et al., 2000, Biotechnol. Prog. 16, 1129-1131; Sheldon, R. A. 2005, Green Chem., 7, 267-278). This discovery has had a great impact over the last six years, as a consequence of the excellent activity and stability displayed by the numerous assayed enzymes. Lipases are the most referenced in both free and immobilized forms (see Madeira Lau R. et al., 2000, Org Lett. 2, 4189-4191; Lozano, P., et al 2001, Biotechnol. Lett. 23, 1529-1533; Lozano, P. et al., 2001, Biotechnol. Bioeng. 75, 563-569). Today, ILs are the most interesting green alternative to volatile organic solvents for development of biocatalytic processes in non aqueous systems, including at extremely high temperatures (i.e. 150° C.) (see Lozano, P. et al., 2003, Biotechnol. Prog. 19, 380-382).

The use of some ILs for the synthesis of biodiesel by using chemical or enzymatic catalysis has recently been described. In all cases, the assayed ILs were based on short-chain 1,3-dialkylimidazolium cations (e.g. 1-ethyl-3-methylimidazolium [Emim], 1-butyl-3-methylimidazolium [Bmim], or 1-hexyl-3-methylimidazolium [Hmim]). Thus, the IL 1-butyl-3-methylimidazolium tetrachloro-indate [Bmim][InCl$_4$] (Neto. et al., 2007, J. Catal. 249, 154-161) has been tested for the synthesis of biodiesel from vegetable oils by using a stannous complex [Sn(3-hydroxy-2-methyl-4-pyrone)$_2$(H$_2$O)$_2$] as chemical catalyst. A fast complete deactivation of the system was observed after the first cycle of use. In the same way, Brönsted acidic ILs (e.g. 1-butylsulfonic-3-methylimidazolium sulphate) have been assayed as chemical catalyst to produce biodiesel by the transesterification of cottonseed oil with methanol at temperatures higher than 150° C. (Wu, Q. et al., 2007, Ind. Eng. Chem. Res., 46, 7955-7960). For the case of enzymatic catalysis, the use of ILs based on short-chain 1,3-dialkylimidazolium cation (i.e. 1-butyl-3-methylimidazolium hexafluorophosphate [Bmim][PF$_6$] or 1-butyl-3-methylimidazolium tetrafluoroborate [Bmim][BF$_4$]) were shown as non fully-appropriate reaction media for the synthesis of biodiesel (Shunitha, S., et al., 2007, Biotechnol. Lett., 29, 1881-1885; Ha, S. H. et al., 2007, Enzyme Microb. Technol., 41, 480-483; Gamba, M. et al., 2008, Adv. Synth. Catal., 350, 160-164). In all cases, the low solubility of triacylglycerides in the assayed ILs resulted in two-phase reaction media that provided low enzymatic activity, ending in 24 h reaction times to reach full conversion of triglycerides into FAMEs.

SUMMARY OF THE INVENTION

One of the aims of the invention is to provide a process for the production of biodiesel using a recyclable solvent with a low environmental impact (green chemistry).

Another aim of the invention is to provide a process for the production of biodiesel with an improved reaction kinetic.

One of the aims of the invention is to provide a process for the production of biodiesel, enabling an easy separation of the reaction products.

Another aim of the invention is to provide a process for the production of biodiesel avoiding the catalyst poisoning.

Another aim of the invention is to provide a process for the production of biodiesel in which different type of oils, fats or fatty acids can be used in the same process.

Another aim of the invention is to provide a process for the production of biodiesel in which presence of water and or free carboxylic acids in the raw oil or fat do not severely impair the process.

The invention relates to the use of a combination of
- at least one ionic liquid which is lipophilic, and non miscible with water, and
- at least one enzyme, for the implementation of an esterification and/or transesterification process of a substrate with at least one alcohol, said substrate consisting of oils, fats, fatty acids, or a mixture thereof, wherein said ionic liquid, said substrate, and said alcohol form a single homogeneous liquid phase at the temperature at which the esterification and/or transesterification process is performed.

In the present invention, the Inventors have surprisingly identified ionic liquids with appropriate carbon chains, which show a good lipophilicity and an appropriate melting temperature which enables the ionic liquid to be liquid at a temperature adequate for an enzymatic esterification and/or transesterification process. This was not obvious because long carbon chains increase the melting temperature of ionic liquids and because enzymes degrade at higher temperatures.

Thus, through the invention, a balance is unexpectedly achieved between the lipophilicity and the melting temperature of the ionic liquid on the one hand and enzymes stability and reactivity on the other hand.

The good lipophilicity of the ionic liquid enables the formation of a single homogenous phase containing said ionic liquid, alcohol and substrate. In other words, the invention relates to the use of an ionic liquid which solubilises the reactants, i.e. the substrates (oils, fats, fatty acids) and the alcohol in order to generate a homogenous liquid phase. The homogenous liquid phase and the enzyme form the reaction phase. The reaction phase:
- is homogeneous, if the enzyme (supported or not) is soluble in the ionic liquid, or
- is a suspension of enzyme within a homogeneous phase, if the enzyme (supported or not) is not soluble in the ionic liquid.

This homogeneous liquid phase presents an advantage in terms of reaction kinetic, because the reaction may occur anywhere in the reaction phase and not only at an interface, as it is in the case of heterogeneous reaction phases.

This single homogeneous liquid phase presents another advantage because it reduces the kinetics of mass transfer that occurs in a liquid-liquid biphasic system.

At the beginning of the reaction, only one homogeneous liquid phase is present, with possibly an enzyme supported or not in suspension within this phase or soluble in this phase.

DETAILED DESCRIPTION OF THE INVENTION

The expression "homogeneous liquid phase" means that the liquid which constitutes said phase is uniform throughout its composition or its structure; in other words, the properties of a smaller part of the solution apply to the whole.

The terms "oils" and "fats" describe chemical compositions containing mainly triacylglycerides and/or diacylglycerides and/or monoacylglycerides and/or other fatty esters (i.e. phospholipids), and carboxylic acids and alcohols of long chains, produced by vegetables or animals and/or by transformation of natural products, being edible or not edible. Typically, oils and fats are lipophilic substances, immiscible with water.

The term "Ionic liquid" (IL) means a liquid which is a salt formed by the association of a cation ($[C]^+$) and an anion ($[A]^-$), being in liquid state at temperatures generally lower than 100° C., and usually equal or lower than room temperature. This has to be compared, for example, to NaCl, which, when heated at a temperature higher than its melting point (>800° C.), is liquid known as a molten salt which may have been considered as an ionic liquid (IL), while an aqueous solution of this salt is an ionic solution (see Wasserscheid, P. and Welton T. Eds., 2003, Ionic Liquids in Synthesis. Wiley-VCH.Verlag). Common ILs are organic onium salts such as phosphonium, sulfonium, tetraalkylammonium cations or any cation resulting from the quaternization of an heterocycle such as imidazolium or pyridinium cations for example, combined with anions having a strong charge delocalization (i.e. $PF_6^-$, $BF_4^-$, bis[(trifluoromethyl)sulfonyl]imide, i.e. $-NTf_2$), or others such as $Cl^-$, $Br^-$, $I^-$, $CF_3-CO_2^-$, $SO_4^{2-}$, $NO_3^-$ etc. From a technological point of view, ILs show interesting physical and chemical properties which allow them to be used as solvents into a great variety of chemical processes (i.e. extraction, reaction media, catalysts, etc. . . . ). These properties include a negligible vapour pressure so that they do not evaporate; an excellent thermal stability (stable at temperatures >300° C. in some cases), as well as their ability to dissolve a wide range of organic and inorganic compounds, including gases and polymers. Additionally, other properties of ILs, such as, density, melting point, polarity and miscibility with water or organic solvents, can be finely tuned as a function of the anion and cation, which structures can be designed at will according to substituents and/or attached functional groups.

The combination may comprise one single ionic liquid or a mixture of ionic liquids. A combination containing one ionic liquid is easier to implement, but if the desired melting temperature or reactant solubilisation properties cannot be achieved with one ionic liquid, a mixture of ionic liquids may be designed to finely reach the desired properties.

The expression "lipophilic" characterises a compound that has an affinity for lipids, tends to combine with lipids, or is capable of dissolving in lipids. Lipophilic compounds invariably have large oil/water partition coefficients. Partition coefficient is the ratio of concentration of a compound (solute) in the two phases of a mixture of two immiscible solvents at equilibrium. Hence, this coefficient is a measure of the differential solubility of the compound between these two solvents, which are generally water and octanol. The logarithm of the ratio of the concentrations of the un-ionized solute in the solvents is called log P:

$$\log P_{oct/wat} = \log\left(\frac{[solute]_{octanol}}{[solute]_{water}^{un-ionized}}\right)$$

In other words, the ionic liquids involved in the invention are hydrophobic.

The expression "hydrophobic" characterises a compound that has no affinity for water; or is tending to repel and not to absorb water; or is tending not to dissolve in water, or not to mix with water, or not to be wetted by water.

In common practice, all the ionic liquids contain a small amount of water.

The term "esterification" designates the general chemical reaction in which two reactants (typically an alcohol and an acid) form an ester and water, as the reaction products. In the present invention, the esterification occurs between the fatty acids and the alcohol (such as methanol or ethanol) to produce fatty acid alkyl esters and water. Said esterification is catalysed by an enzyme chosen among lipases, phospholipases and esterases.

The term "transesterification" designates the chemical reaction in which the alcoxy group of an ester compound is exchanged with another alcoxy group via the reaction of said ester with an alcohol, usually in presence of a catalyst. In the present invention, a transesterification occurs between triglycerides, or diglycerides, or monoglycerides and an alcohol (such as methanol or ethanol) catalysed by an enzyme, to produce fatty acid alkyl esters and glycerol.

According to another embodiment, the invention relates to a combination, such as here above defined, wherein said ionic liquid is
hydrophobic,
solid at room temperature,
non miscible with glycerol,
wherein said ionic liquid, said substrate, and said alcohol form a single homogeneous liquid phase at the temperature at which the esterification and/or transesterification process is performed.

As the reaction goes on, new compounds are formed, substantially biodiesel and glycerol. At the end of the reaction, when all the reactants have been consumed by the reaction, new phases have been formed, which contain respectively the reaction products which have been formed, said new phases being distinct from the phase containing the ionic liquid.

According to another embodiment, the invention relates to a combination, such as here above defined, wherein three phases are formed at the end of said esterification and/or transesterification process,
a first phase containing at least one ionic liquid, and at least one enzyme,
a second phase consisting substantially of glycerol,
a third phase consisting substantially of fatty acid alkyl esters.

According to another embodiment, the invention relates to a combination, such as here above defined, wherein three phases are formed at the end of said esterification and/or transesterification process,
a first phase containing at least one ionic liquid, and at least one enzyme,
a second phase consisting substantially of glycerol,
a third phase consisting substantially of fatty acid alkyl esters.

According to another embodiment, the invention relates to a combination, such as here above defined, wherein three phases are formed at the end of said esterification and transesterification process,
a first phase containing at least one ionic liquid, and at least one enzyme,
a second phase consisting substantially of glycerol,
a third phase consisting substantially of fatty acid alkyl esters.

At the end of the reaction, when at least one of the reactants has been consumed in the reaction, new products are formed. Theses new products are:
fatty acid alkyl esters, or a mixture of fatty acid alkyl esters, resulting from the transesterification of triglycerides, diglycerides and monoglycerides with an alcohol, and from the esterification of fatty acid with an alcohol, and
water and
glycerol.

Glycerol and fatty acid alkyl esters are not soluble in each other, and both are not soluble in the phase containing the ionic liquid. Thus, three phases are formed at the end of the reaction,
an ionic liquid phase comprising the enzyme,
a glycerol phase,
a fatty acid alkyl ester phase.

The expression "first phase containing" means that the considered first phase is constituted by the ionic liquid, the enzyme, and the substrate and/or the alcohol that remain unconsumed at the end of the reaction. If the alcohol amount is stoichiometric with respect to the substrate amount, then the first phase is composed of at least 90%, or 95%, or 99% of ionic liquid and enzyme, at the end of the reaction.

The expression "second phase consisting substantially of glycerol" means that the considered second phase is composed of at least 90%, or 95%, or 99% of glycerol at the end of the reaction. The rest may be constituted by water, alcohol, or polar impurities (substrate may originate from wastes and thus may contain traces of unknown compounds).

The possible presence of alcohol results from an excess of alcohol which has not reacted with the substrate.

The expression "third phase consisting substantially of fatty acid alkyl esters" means that the considered third phase is composed of at least 90%, or 95%, or 99% of fatty acid alkyl esters at the end of the reaction. The rest may be constituted by fatty acids or apolar impurities (substrate may originate from wastes and thus may contain traces of unknown compounds).

The expression "miscible" means the property of liquids to mix in all proportions, forming a homogeneous solution. By contrast, two liquids are said to be immiscible if in any proportion, they do not form a solution. Miscibility is different from solubility.

The expression "solubility" refers to the ability of a given substance, the solute, to dissolve in a solvent. It is measured in terms of the maximum amount of solute dissolved in a solvent at equilibrium. Some liquids are soluble in any proportion within a given solvent; this is known as miscibility. Thus, miscible liquids are soluble in one another, but liquid which are soluble in one another are not necessarily miscible.

According to other embodiment, the ionic liquid used in the invention can be
solid or liquid at 0° C., or
solid or liquid at room temperature.

According to an advantageous embodiment, the invention relates to the use of a combination, such as here above defined, wherein said ionic liquid is liquid or solid at room temperature, preferably solid at room temperature.

According to another advantageous embodiment, the invention relates to the use of a combination, such as here above defined, wherein said ionic liquid is solid at 0° C.

According to another advantageous embodiment, the invention relates to the use of a combination, such as here above defined, wherein said ionic liquid is liquid or solid at room temperature, preferably solid at room temperature.

The ionic liquid is advantageously liquid at the reaction temperature (generally about 50 to about 60° C.) and solid at 0° C. The ionic liquid may be solid or liquid between these two temperatures, for instance at room temperature.

The expression "room temperature" means a temperature range commonly found in building situated in temperate regions, this ranging from about 10° C. to about 40° C., usually from about ° C. to about 30° C.

If the ionic liquid is solid at 0° C. and solid at room temperature, heat is needed in order to reach the ionic liquid melting temperature so that the reaction can proceed in a liquid phase.

If the ionic liquid is solid at 0° C. and liquid at room temperature,
the reaction can proceed without heating, but the reaction kinetic will be lower and the fatty acids alkyl esters will be produced slowly, or
the reaction can be heated in order to increase the reaction kinetic and to increase the fatty acids alkyl esters production rate.

The expression "melting temperature" means the temperature range at which a compound state changes from solid to liquid. Although this would suggest a specific temperature, most crystalline compounds actually melt over a range of a few degrees or less. At the melting temperature, or melting point, the solid and liquid phases coexist in equilibrium.

The reaction temperature can range from room temperature (i.e. 30° C.) to 50° C. This range is less advantageous, as the reaction process will be longer because of the low heating energy and thus low kinetic of the reaction.

The reaction temperature can range from 50° C. to 70° C. This range is advantageous, as it does not involve too much energy and the heating will increase the reaction kinetic without causing too much degradation of the enzyme.

The reaction temperature can range from 70° C. to 100° C. This range is less advantageous, as it involves more energy and the temperature may reduce the enzyme stability.

According to another embodiment, the invention relates to the use of a combination, such as here above defined, with an organic solvent or an ionic liquid, wherein said combination has a melting temperature higher than room temperature and said combination is liquid at room temperature.

One or several organic solvents (e.g. acetonitrile, tetrahydrofuran) may be added to the said combination in order to modify the melting temperature of the ionic liquid. Generally, the melting temperature will be decreased, and thus ionic liquids, which are not liquid on their own at the reaction temperature, can be used.

One or several ionic liquids may be added to the said combination in order to modify the melting temperature of the ionic liquids and enzyme mixture thus obtained. The melting temperature will be decreased, and thus ionic liquids, which are not liquid on their own at the reaction temperature, can be used.

According to an advantageous embodiment, the invention relates to the use of a combination, such as here above defined, wherein said ionic liquid, said substrate, and said alcohol form a single homogeneous liquid phase, at room temperature, preferably at a temperature higher than 30° C.

A homogenous liquid phase is advantageous, as it ensures a good three dimensional homogeneous repartition of the reaction components through the reaction phase, and an optimal probability of contact between the reaction components. Thus the reaction can proceed in the best condition to achieve a high yield.

According to another advantageous embodiment, the invention relates to the use of a combination, such as here above defined, for the implementation of fatty acid alkyl ester producing process through an esterification and/or transesterification reaction of the substrate.

Fatty acid alkyl esters are produced through an esterification of the fatty acids, and through a transesterification of the mono, di and triacylglycerides present in oils and fats used in the reaction. These esters can be used as biodiesel.

According to an advantageous embodiment, the invention relates to the use of a combination, such as here above defined, wherein the enzyme is supported, and said supported enzyme is in suspension, or soluble, within said single homogeneous liquid phase.

The expression "supported enzyme" means that the enzyme is combined with a carrier, said carrier being inert with respect to the compounds (alcohol, substrate, ionic liquid) present in the homogeneous liquid phase, and the enzyme being generally physical or chemically (i.e. by adsorption, covalent linkage, etc) attached onto the surface of the carrier.

The expression "suspension" means that particles are immersed into a homogeneous liquid and thus form a heterogeneous mixture. Said particles may be large enough for sedimentation.

A supported enzyme is generally easy to remove from the ionic liquid phase, as it is not soluble in the ionic liquid and remains in suspension within the homogeneous liquid phase.

According to another embodiment, the invention relates to the use of a combination, such as here above defined, wherein the enzyme is not supported, and said non supported enzyme is in suspension, or soluble, within the said single homogeneous liquid phase.

Non supported enzymes may be soluble in the ionic liquid and thus the reaction phase remains completely homogeneous.

According to an advantageous embodiment, the invention relates to the use of a combination, such as here above defined, wherein the ionic liquid melting temperature is lower than the temperature of the esterification and/or transesterification process, and preferably the ionic liquid melting temperature being within the temperature range from about 0° C. to about 100° C., particularly from 0° C. to 40° C., and from 40° C. to 60° C., and from 60° C. to 100° C.

According to an advantageous embodiment, the invention relates to the use of a combination, such as here above defined, wherein the melting temperature of a mixture of said combination with a substrate is higher than the melting point of said substrate alone, said substrate consisting of oils, fats, fatty acids, or a mixture thereof.

Interestingly and surprisingly, it has been observed that the melting point of an ionic liquid may be increased when solubilised in oil (for example $[C_{16}MIM][PF_6]$ in triolein and $[C_{18}MIM][PF_6]$ in triolein). An increase in the melting point would require more energy to obtain a liquid homogeneous initial phase. The enzyme is less stable at high temperature, thus it is preferable not to increase too much the reaction temperature.

Melting points of several ionic liquids according to the present invention are indicated in the table below:

| Short Name | Name | Melting Point (° C.) |
|---|---|---|
| $C_{12}$mim $BF_4$ | 1-Dodecyl-3-methylimidazolium Tetrafluoroborate | 30 |
| $C_{14}$mim $BF_4$ | 1-Tetradecyl-3-methylimidazolium Tetrafluoroborate | 36 |
| $C_{16}$mim BF4 | 1-Hexadecyl-3-methylimidazolium Tetrafluoroborate | 49 |
| $C_{18}$mim BF4 | 1-Octadecyl-3-methylimidazolium Tetrafluoroborate | 60 |
| $C_{12}$mim $PF_6$ | 1-Dodecyl-3-methylimidazolium Tetrafluoroborate | 58 |
| $C_{14}$mim $PF_6$ | 1-Tetradecyl-3-methylimidazolium Tetrafluoroborate | 67 |
| $C_{16}$mim PF6 | 1-Hexadecyl-3-methylimidazolium Tetrafluoroborate | 74 |
| $C_{18}$mim $PF_6$ | 1-Octadecyl-3-methylimidazolium Hexafluorophosphate | 82 |
| $C_{14}$mim $NTf_2$ | 1-Tetradecyl-3-methylimidazolium Bistriflimide | 33 |
| $C_{16}$mim $NTf_2$ | 1-Hexadecyl-3-methylimidazolium Bistriflimide | 46 |
| $C_{18}$mim $NTf_2$ | 1-Octadecyl-3-metylimidazolium Bistriflimide | 53 |

According to another advantageous embodiment, the invention relates to the use of a combination, such as here above defined, wherein the lipophilic ionic liquid is constituted by a cation and an anion, said cation being constituted by a cationic head, and said anion being constituted by an anionic head, and wherein said cationic head and/or anionic head are eventually substituted by one or several carbon side chains which may be similar or different from each other.

The expression "head" means the part of the ion that carries the electrical charge, depending on the ion considered, it can be:

a single atom (i.e. cations like lithium, sodium, potassium, cesium, or anions like fluoride, chloride, bromide, iodide), or a group of atoms (i.e. $PF_6^-$, bis(trifluoromethylsulfonyl) imide ($NTf_2^-$) $BF_4^-$, tris(pentafluoroethyl)trifluorophosphate (FAP), alkylsulfates, alkyl group including 1 to 10 carbon atoms, or an heteroaromatic ring (i.e. imidazolium, pyridinium, triazolium)

onium cations such as pyrrolidinium, guanidinium, sulfonium, phosphonium or ammonium cations.

The expression "carbon side chain" describes chain of carbon atoms, linear or branched, covalently linked to the head, said carbon side chains are not carrying the electrical charge of the ion (i.e. alkyl chains).

For instance, in the tetrabutyl ammonium cation ($Bu_4N^+$), the cationic head is the nitrogen atom and the four butyl chains are four carbon side chains.

The ionic liquid may be constituted by a hydrophobic cation (i.e. 1,3-Dialkylimidazolium, Tetraalkylammonium) and a hydrophobic anion (i.e. $PF_6^-$, $BF_4^-NTf_2^-$, FAP).

The ionic liquid may be constituted by a hydrophilic cation (i.e; choline, butyrobetaine, $Me_4N^+$, $Li^+$) and a hydrophobic anion.

The ionic liquid may be constituted by a hydrophobic cation and a hydrophilic anion (i.e. acetate, methylsulfate, chloride, bromide, fluoride . . . ).

The lipophilicity is related to the substitution of the anionic head or cationic head by carbon side chains.

A hydrophobic cation, the cationic head of which is substituted by one or several carbon side chains as defined above, is hydrophobic and lipophilic (i.e. ammonium, imidazolium, pyridinium).

A hydrophobic anion, the anionic head of which is substituted by one or several carbon side chains as defined above, is hydrophobic and lipophilic (i.e. $RSO_3^-$, R representing the carbon side chain).

It is advantageous for the ionic liquid to be constituted of a lipophilic cation and a hydrophobic anion.

According to an advantageous embodiment, the invention relates to the use of a combination, such as here above defined, wherein the carbon side chain on the cationic head and/or anionic head are linear or branched, saturated or unsaturated carbon chains, providing at least one of the side chain comprise at least 10 carbon atoms, preferably at least 12, 13, 14, 15 carbon atoms, and in particular at least 16, 17, 18 carbon atoms.

Long carbon chains increase the lipophilicity of the ionic liquid, but also increase its melting temperature. It is not obvious to find an appropriate balance between these two criteria, and keep the melting point of the ionic liquid in a temperature range suitable for an enzymatic reaction.

In the present invention, the Inventors have unexpectedly identified that ionic liquids with carbon side chains comprising 12 to 15, or preferably 16 to 18 carbon atoms, show a good lipophilicity and an appropriate melting temperature.

It is important to note that the preferable carbon side chain length may vary depending on the substrate nature. Most natural oils produced in industrial scale have 16 or 18 carbon long side chains. For this type of substrate, ionic liquids with 16 to 18 carbon atoms side chains are preferred because of their good substrate solubilisation properties.

Substrates with short carbon chains, such as 15, 14, 13 or 12 carbon atoms, may be more soluble in ionic liquids with carbon side chains shorter than 18 carbon atoms, such as 15, 14, 13 or 12 carbon atoms.

The expression "saturated and unsaturated" means the carbon side chains can include single bond(s), double bond(s), triple bond(s), cycle, aromatic cycle(s), heteroaromatic cycle (s). Insaturation relates to any structure which may be subjected to reduction.

According to another embodiment, the invention relates to the use of a combination, such as hereabove defined, wherein said carbon side chains are substituted by at least one functional group chosen among alkylether, nitrile, cyanoalkyl, alkylsulfonyl, alkylthioether.

According to another advantageous embodiment, the invention relates to the use of a combination, such as here above defined, wherein the ionic liquid cation is chosen among imidazolium, pyridinium, triazolium, pyrrolidinium, guanidinium, sulfonium, phosphonium or ammonium cations, substituted by at least one lipophilic carbon side chain comprising at least 10 carbon atoms.

According to an advantageous embodiment, the invention relates to the use of a combination, such as here above defined, wherein the ionic liquid anion is chosen among $PF_6^-$, bis(trifluoromethylsulfonyl)imide ($NTf_2^-$) $BF_4^-$, tris(pentafluoroethyl)trifluorophosphate (FAP), alkylsulfate with an alkyl chain from 1 to 20 carbon atoms, alkylsulfonate with an alkyl chain from 1 to 20 carbon atoms, $Cl^-$, $I^-$, $Br^-$, or dialkylphosphate with alkyl chains from 1 to 20 carbon atoms, preferably chosen among $NTf_2^-$, $PF_6^-$, alkylsulfates with an alkyl chain from 1 to 20 carbon atoms, preferably $NTf_2^-$ or FAP, and in particular $NTf_2^-$.

According to another advantageous embodiment, the invention relates to the use of a combination, such as here above defined, wherein the ionic liquid is chosen among 1-methyl-3-octadecylimidazolium bis(trifluoromethylsulfonyl)imide, 1-hexadecyl-3-methylimidazolium bis(trifluoromethylsulfonyl)imide, trimethyloctylammonium (bis(trifluoromethylsulfonyl)imide.

The ionic liquids described in the present invention are neutral with respect to their pH. The term "neutral pH" designates a pH ranging from about 6.8 to about 7.4. The pH range varying from 6.8 to 7.4 corresponds to a physiological pH.

The pH of the final combination is important. The fatty acids alkyl esters produced (i,e the biodiesel) should contain as little acids or bases as possible and be below 2%, preferentially below 1%, preferentially they should be free of acids or bases. The presence of large amounts of acids or bases would require further washings of the final product (fatty acids alkyl esters) with water, and thus increase the water content of the fatty acids alkyl esters, and increase the cost of the process.

According to another embodiment, the invention relates to the use of a combination, such as here above defined, wherein the enzyme is a lipase or an esterase, preferably a lipase chosen among the group consisting of *Candida antartica, Candida rugosa, Candida cylindracea, Pseudomonas cepacia, Mucor miehei, Mucor javaicus, Aspergillus niger*, swine pancreas, *Aspergillus subtilis, Bacillus subtilis, Aspergillus orayze, Rhyzopus oryzae, Chromobacterium visocosum, Yarrowia lipolitica, Thermus lanuginose*, pig liver, particularly a lipase B from *Candida Antartica*.

The expressions "lipase" and "esterase" designate enzymes which catalyse the hydrolysis, esterification and transesterification reaction of lipids or other naturally occurring esters. Whether the reaction is a hydrolysis or an esterification (or transesterification) depends on the concentration of water and alcohol which are present. In living organisms, water is present in large quantities so that the catalysed reaction is mainly hydrolysis. In the present invention, water is present in minute amounts as compared to the alcohol amount; thus the catalysed reaction is mainly the esterification of present fatty acids and the transesterification of esters.

According to an advantageous embodiment, the invention relates to the use of a combination, such as here above defined, wherein the substrate is chosen among animal fats, sunflower seed oil, soybean oil, palm oil, coconut oil, flax seed oil, rape seed oil, corn oil, cotton seed oil, ground nut oil, canola oil, olive oil, castor oil, jatropha oil, waste edible and non-edible oils (i.e. wastes of vegetable oils and animal fats from industrial kitchen processes, fat wastes from pork industry, fat wastes from fish factories), and mixture thereof.

According to another advantageous embodiment, the invention relates to the use of a combination, such as here above defined, wherein the substrate is an association of at least two different substrates.

According to another advantageous embodiment, the invention relates to the use of a combination, such as here above defined, wherein the substrate contains triglycerides, diglycerides, monoglycerides, phospholipids, and mixture thereof.

Waste oils and fats and natural oils and fats often contain a mixture of glycerides (i.e. triglycerides, diglycerides, and monoglycerides). Thus it is advantageous to be able to proceed with bulk oils and fats instead of refined oils and fats which contain only one type of glycerides.

The present invention enables to process a mixture of different glycerides and fatty acids into biodiesel.

According to an advantageous embodiment, the invention relates to the use of a combination, such as here above defined wherein the substrate contains in volume at least 30%, in particular 50%, preferably more than 70% of triglycerides.

The proportion of triglycerides in the mixture of glycerides and fatty acids composing the substrate may vary, depending on the source of the substrate.

Oils and fats unrefined, such as waste or bulk oils and fats, are cheaper. Thus, it is commercially advantageous for a biodiesel production process to proceed with crude oils and fats containing different components eventually in large proportion.

Biodiesel yield will be proportional to the fatty acyl chains (esterified with glycerol in the case of triglycerides, diglycerides and monoglycerides, and non esterified in the case of fatty acids) content of the substrates assayed.

According to an advantageous embodiment, the invention relates to the use of a combination, such as here above defined, wherein the substrate contains in volume a water content lower than 10% of water, in particular 2% of water, preferably 0.5% of water.

Water is an undesirable product in the esterification described in the present invention, because water may interact with the enzyme and reduce its catalytic activity.

Water may also produce fatty acids upon hydrolysis of the glycerides or biodiesel. As the proportion of water increases, this side reaction becomes more important and can increase the length of the process and/or reduce the process yield.

Fatty acids may also generate micelles and/or act as surfactants compounds, which disrupt the phase separation.

According to another embodiment, the invention relates to the use of a combination, such as here above defined, wherein the alcohol is selected from the group consisting of alcohols having from 1 to 4 carbon atoms, in particular methanol, ethanol, propanol, butanol, isomers thereof, and mixture thereof, particularly methanol.

According to another advantageous embodiment, the invention relates to the use of a combination, such as here above defined, wherein the ionic liquid is liquid at the temperature at which the esterification and/or transesterification process is performed,
the ionic liquid is miscible with the substrate,
the ionic liquid is miscible with said alcohol, and
the ionic liquid is miscible with a mixture of the substrate and said alcohol.

It is advantageous to have a good separation between the three different phases at the end of the reaction, because the separation of the three phases by decantation is easier. This immiscibility feature is related to the particular structure of the ionic liquid.

According to an advantageous embodiment, the invention relates to the use of a combination, such as here above defined, wherein the ionic liquid is immiscible with glycerol formed during the esterification and/or transesterification reaction of the substrate with at least one alcohol, and the ionic liquid is immiscible with fatty acid alkyl esters.

In the present invention, the ionic liquid is miscible with the alcohol and the substrate, thus a homogeneous liquid phase is generated at the beginning of the process.

The ionic liquid is immiscible with glycerol and the fatty acid alkyl ester (FAAE) produced by the enzymatic reaction, and the FAAE and glycerol newly generated are also immiscible in one another, thus three phases are formed. During the esterification and/or transesterification reaction some intermediate compounds such as monoglycerides, diglycerides or fatty acids are obtained. These intermediate compounds may solubilise small amounts of glycerol or FAAE in one another, or in the ionic liquid. At the end of the reaction, when all intermediate compounds are consumed, the three phases are clearly defined and can be easily separated.

Most of the natural fats and oils are composed of triglycerides; these triglycerides are transesterified to diglycerides and FAAE, then diglycerides to monoglycerides and FAAE, and then monoglyceride to FAAE and glycerol.

The traces of water present in the reaction may generate some fatty acids by hydrolysis of triglycerides, diglycerides, monoglycerides or FAAE. As the alcohol is present in a very large amount compared to water, the equilibrium between hydrolysis and esterification (and transesterification) is in favour of the esterification (and transesterification) reaction. Furthermore the enzymes catalyse esterification reaction of the fatty acids into FAAE, thus fatty acids are generated in minute amounts and are converted to FAAE.

When the reaction is complete, all the triglycerides, diglycerides, monoglycerides and fatty acids are converted in FAAE, thus triglycerides, diglycerides, monoglycerides and fatty acids can be considered as intermediate products between the triglyceride and the FAAE.

According to another embodiment, the invention relates to a final combination, comprising the following three phases, at room temperature,
- a first phase, in a solid state, containing at least one ionic liquid, and at least one enzyme,
- a second phase, in a liquid state, consisting substantially of glycerol,
- a third phase, in a liquid state, consisting substantially of fatty acid alkyl esters.

The term "final combination" designates the combination that remains when all the substrate that has been introduced in the reaction mixture is esterified or transesterified to fatty acid alkyl esters According to another embodiment, the invention relates to a final combination, such as here above defined, wherein said ionic liquid is
- hydrophobic,
- solid at room temperature,
- non miscible with glycerol,
- comprising the following three phases, at room temperature,
- a first phase, in a solid state, containing at least one ionic liquid, and at least one enzyme,
- a second phase, in a liquid state, consisting substantially of glycerol,
- a third phase, in a liquid state, consisting substantially of fatty acid alkyl esters.

According to another embodiment, the invention relates to a final combination, such as here above defined, wherein said ionic liquid is
- hydrophobic,
- solid at room temperature,
- wherein said ionic liquid, said substrate, and said alcohol form a single homogeneous liquid phase at the temperature at which the esterification and/or transesterification process is performed,
- comprising the following three phases, at room temperature,
- a first phase, in a solid state, containing at least one ionic liquid, and at least one enzyme,
- a second phase, in a liquid state, consisting substantially of glycerol,
- a third phase, in a liquid state, consisting substantially of fatty acid alkyl esters.

According to another embodiment, the invention relates to a final combination, such as here above defined, wherein said ionic liquid is
- hydrophobic,
- non miscible with glycerol,
- wherein said ionic liquid, said substrate, and said alcohol form a single homogeneous liquid phase at the temperature at which the esterification and/or transesterification process is performed,
- comprising the following three phases, at room temperature,
- a first phase, in a solid state, containing at least one ionic liquid, and at least one enzyme,
- a second phase, in a liquid state, consisting substantially of glycerol,
- a third phase, in a liquid state, consisting substantially of fatty acid alkyl esters.

According to another embodiment, the invention relates to a final combination, such as here above defined, wherein said ionic liquid is
- solid at room temperature,
- non miscible with glycerol,
- wherein said ionic liquid, said substrate, and said alcohol form a single homogeneous liquid phase at the temperature at which the esterification and/or transesterification process is performed,
- comprising the following three phases, at room temperature,
- a first phase, in a solid state, containing at least one ionic liquid, and at least one enzyme,
- a second phase, in a liquid state, consisting substantially of glycerol,
- a third phase, in a liquid state, consisting substantially of fatty acid alkyl esters.

According to another embodiment, the invention relates to a final combination, such as here above defined, wherein said ionic liquid is
- hydrophobic,
- solid at room temperature,
- non miscible with glycerol,
- wherein said ionic liquid, said substrate, and said alcohol form a single homogeneous liquid phase at the temperature at which the esterification and/or transesterification process is performed,
- comprising the following three phases, at room temperature,
- a first phase, in a solid state, containing at least one ionic liquid, and at least one enzyme,
- a second phase, in a liquid state, consisting substantially of glycerol,
- a third phase, in a liquid state, consisting substantially of fatty acid alkyl esters.

The invention relates to a process for the esterification and/or transesterification of a substrate, said substrate consisting of oils, fats, fatty acids, or a mixture thereof, into esters comprising an initialization step consisting in:
- bringing together at least one substrate, at least one alcohol, and at least one enzyme in at least one ionic liquid, said substrate, alcohol, and ionic liquid forming a single homogeneous liquid phase at the temperature at which the process is performed, said alcohol and substrate being in appropriate amount to form esters, The substrate, the alcohol, the enzyme and the ionic liquid are the four components of the reaction. They can be introduced in any order. However, alcohols (i.e. methanol or ethanol) are known by the man skilled in the art to impair the catalytic activity of the enzymes. Thus, when the enzyme and the alcohol are the two first components brought together, they should be quickly diluted in another component (i.e. substrate, ionic liquid) in order to protect the enzyme from the deleterious effect of the alcohol.

In a preferred embodiment, the ionic liquid is introduced first, then the alcohol, then the substrate, and lastly the enzyme. This sequence enables a good solubilization of the alcohol within the ionic liquid before the substrate is added, which may reduce the viscosity of the system, may reduce the melting point of the IL, and may prevent an inactivation of the enzyme by the alcohol.

According to another embodiment, the invention relates to a process, such as here above defined, for the esterification and/or transesterification of the substrate into esters comprising an additional recovery step consisting in:
  recovering the esters formed in the esterification and/or transesterification reaction, and possibly recovering the glycerol formed in the esterification and/or transesterification reaction.

The invention relates to a process for the esterification and/or transesterification of a substrate, said substrate consisting of oils, fats, fatty acids, or a mixture thereof, into fatty acid alkyl esters, comprising an initialization step consisting in:
  bringing together at least one substrate, at least one alcohol, and at least one enzyme in at least one ionic liquid, said substrate, alcohol, and ionic liquid forming a single homogeneous liquid phase, said alcohol and substrate being in appropriate amounts to form fatty acid alkyl esters, wherein said ionic liquid is liquid at the temperature at which the process is performed.

The expression "appropriate amounts" means that the molar ratio of alcohol and substrate are suited for the complete esterification or transesterification of the substrate. Typically, one considers the substrate to be formed mainly by triglycerides, thus requiring three equivalents of alcohol for a complete esterification or transesterification. However, an excess of alcohol compared to the substrate is often required in order to enhance the reaction kinetic. A molar ratio of alcohol to substrate inferior to 1:1 (less alcohol than substrate in mole) leads to an incomplete esterification or transesterification, thus an incomplete reaction.

According to an advantageous embodiment, the invention relates to a process, such as here above defined, for the esterification and/or transesterification of the substrate into fatty acid alkyl esters comprising an additional recovery step consisting in:
  recovering the fatty acid alkyl esters formed in the esterification and/or transesterification reaction, and possibly recovering the glycerol formed in the esterification and/or transesterification reaction The expression "recovering" means that the fatty acid alkyl esters formed in the esterification and/or transesterification reaction, and possibly the glycerol formed in the transesterification reaction, are isolated from the reaction phase. This isolation, or separation, can be performed by any means known by the man skilled in the art to perform a liquid-liquid separation.

According to another advantageous embodiment, the invention relates to a process, such as here above defined, for the esterification and/or transesterification of the substrate into fatty acid alkyl esters comprising an additional restoration step consisting in recovering and possibly purifying the combination of ionic liquid and enzymes.

The expression "restoration" means isolating, and if necessary purifying, the ionic liquid and enzyme combination. The combination can be recycled at the end of the reaction in order to be reused in another reaction. For this purpose, the combination has to be separated from other products (i.e. impurities) that could decrease the reaction yield in the next esterification and/or transesterification reaction.

According to another embodiment, the invention relates to a process, such as here above defined, for the esterification and/or transesterification of the substrate into fatty acid alkyl esters comprising an additional recovery step consisting in recovering:
  the phase consisting substantially of fatty acid alkyl esters, and
  the phase consisting substantially of glycerol.

According to an advantageous embodiment, the invention relates to a process, such as here above defined, for the esterification and/or transesterification of the substrate into fatty acid alkyl esters comprising:
  an initialization step, consisting in
    bringing together at least one substrate, at least one alcohol, and at least one enzyme in at least one ionic liquid, said substrate, alcohol, and ionic liquid forming a single homogeneous liquid phase at room temperature or preferably at a temperature higher than 30° C., said alcohol and substrate being in appropriate amount to form fatty acid alkyl esters, and
  a recovery step, consisting in recovering:
    the phase consisting substantially of the fatty acid alkyl esters formed in the esterification and/or transesterification reaction, and
    the phase consisting substantially of the glycerol formed in the esterification and/or transesterification reaction, and
    the phase consisting essentially of ionic liquid and enzyme, said ionic liquid being either liquid or solid preferably solid at room temperature, and
  a restoration step, consisting in recovering and purifying the combination of ionic liquid and enzymes, to obtain a purified combination of ionic liquid and enzymes.

According to another advantageous embodiment, the invention relates to a process, such as here above defined, for the esterification and/or transesterification of the substrate into fatty acid alkyl esters comprising:
  a reaction step, consisting in
    bringing together at least one substrate, said substrate consisting of oils, fats, fatty acids, or a mixture thereof, at least one alcohol, in a combination of at least one ionic liquid and at least one enzyme, said substrate, alcohol, and ionic liquid forming a single homogeneous liquid phase, said alcohol and substrate being in appropriate amount to form fatty acid alkyl esters, wherein said ionic liquid is liquid at the temperature at which the process is performed, and
  a recovery step, consisting in recovering:
    the phase consisting substantially of the fatty acid alkyl esters formed in the esterification and/or transesterification reaction, and
    the phase consisting substantially of the glycerol formed in the esterification and/or transesterification reaction, and
  a restoration step, consisting in
    recovering and purifying the combination of ionic liquid and enzymes, to obtain a purified combination of ionic liquid and enzymes,
  with the three said steps defined above forming a cycle.

The expression "cycle" means a full reaction process, which comprises:
  mixing the reaction components (ionic liquid, enzyme, substrate, alcohol) together, and performing the reaction for a time long enough to get as much as possible, with respect to the starting materials, fatty acid alkyl esters, and separating the reaction products from the ionic liquid phase, and processing the ionic liquid and enzyme combination, in order to reuse the combination in another reaction.

The ionic liquid and enzyme combination can be reused. Only the combination may be or is in common from one cycle to another, the alcohol and the substrate being added for each cycle.

The numbering of a cycle corresponds to the number of times in which the above defined combination is used plus one.

For example, the fourth cycle corresponds to an above mentioned combination which has been recycled 3 times.

According to an advantageous embodiment, the invention relates to a process, such as here above defined, for the esterification and/or transesterification of the substrate into fatty acid alkyl esters comprising a step of implementing at least one cycle, preferably repeating said cycle at least 7 times, and in each given cycle, the combination of the ionic liquid and of at least one enzyme used in the reaction step is the purified combination of the ionic liquid and of the enzyme obtained at the end of the restoration step involved in the cycle preceding a given cycle.

When a reaction is finished, the fatty acid alky esters and glycerol are isolated, and the ionic liquid and enzyme combination is purified. Then another cycle starts using the purified ionic liquid and enzyme combination, and new batches of substrate and alcohol.

For each new cycle, the combination is recycled from the previous cycle combination, and new batches of substrate and alcohol are added in order to produce fatty acid alkyl esters and glycerol.

According to another embodiment, the invention relates to a process, such as here above defined, for the esterification and/or transesterification of the substrate into fatty acid alkyl esters wherein said cycles are repeated until the catalytic activity of the enzyme is exhausted, leading to an exhausted enzyme.

The expression "catalytic activity" means the capacity of the enzyme to catalyse a chemical transformation. Virtually, enzymes can transform an infinite number of reactants (or set of reactants) according to one type of reaction. Because of external conditions such as temperature, or impurities that interact with the enzymes, the enzymes slowly denature and the conformation of their active site is impaired, thus their ability to catalyse chemical reaction. Over the time, and because they are exposed to harsh conditions, enzymes loose their activity.

When no more active enzymes can be found, or if a large proportion of the enzymes have lost their activity, they are considered as "exhausted". The distinction between active enzymes and exhausted enzymes is subject to the appreciation of the man running the process catalysed by the said enzymes.

Typically, the more the enzymes in the process are exhausted, the longer the reaction time is. At a certain point, the reaction will be too slow and the enzymes will be considered as exhausted.

According to an advantageous embodiment, the invention relates to a process, such as here above defined, comprising a step of discarding the exhausted enzyme from the ionic liquid to give a regenerated ionic liquid.

The expression "Discarding" means the removal of the enzymes from the combination of the ionic liquid and of the enzymes. It is a purification of the ionic liquid from exhausted enzymes. The regenerated ionic liquid obtained can be reused in the next cycle, and upon addition of active enzymes, a new combination is formed with the regenerated ionic liquid.

According to another advantageous embodiment, the invention relates to a process, such as here above defined, wherein three phases are formed at the end of the said esterification and/or transesterification process, a first phase consisting substantially of at least one ionic liquid, and at least one enzyme, a second phase consisting substantially of glycerol, a third phase consisting substantially of fatty acid alkyl esters.

According to an advantageous embodiment, the invention relates to a process, such as here above defined, wherein said ionic liquid is solid at room temperature.

According to another advantageous embodiment, the invention relates to a process, such as here above defined, wherein said ionic liquid is solid at 0° C.

According to another advantageous embodiment, the invention relates to a process, such as here above defined, wherein said ionic liquid is liquid at room temperature.

According to an advantageous embodiment, the invention relates to a process, such as here above defined, wherein said combination with a melting temperature higher than room temperature is mixed with an organic solvent or an ionic liquid, to give a mixture which is liquid at room temperature.

According to another embodiment, the invention relates to a process, such as here above defined, wherein said ionic liquid said substrate, and said alcohol form a single homogeneous liquid phase, at room temperature.

According to an advantageous embodiment, the invention relates to a process, such as here above defined, wherein said enzyme is supported, and said supported enzyme is in suspension, or soluble, within the said single homogeneous liquid phase.

According to another advantageous embodiment, the invention relates to a process, such as here above defined, wherein said enzyme is not supported, and said non supported enzyme is in suspension, or soluble, within the said single homogeneous liquid phase.

According to an advantageous embodiment, the invention relates to a process, such as here above defined, wherein the ionic liquid melting temperature is lower than the temperature of the esterification and/or transesterification or esterification and/or transesterification process, and preferably the ionic liquid melting temperature being within the temperature range of about 0° C. to about 100° C., particularly above 40° C., in particular above about 40° C. and below about 80° C.

According to another embodiment, the invention relates to a process, such as here above defined, wherein the hydrophobic ionic liquid is constituted by a cation and an anion, said cation being constituted by a cationic head, and said anion being constituted by an anionic head, and wherein said cationic head and/or anionic head are eventually substituted by one or several carbon side chains which may be similar or different from each other, and said carbon chains having at least 10 carbon atoms, preferably at least 12, 13, 14, 15 carbon atoms, and in particular at least 16, 17, 18 carbon atoms.

According to another advantageous embodiment, the invention relates to a process, such as here above defined, wherein the carbon side chains on the cationic head and/or anionic head are linear or branched, saturated or unsaturated carbon chains, providing at least one of the side chains comprises at least 10 carbon atoms, preferably at least 12, 13, 14, 15 carbon atoms, and in particular at least 16, 17, 18 carbon atoms.

According to an advantageous embodiment, the invention relates to a process, such as here above defined, wherein said cationic head and/or anionic head are substituted by at least one carbon group, particularly aromatic or aliphatic cycle, alkane, alkene, or alkyne.

According to another advantageous embodiment, the invention relates to a process, such as here above defined, wherein the ionic liquid cationic head is chosen among imidazolium, pyridinium, triazolium, pyrrolidinium, guanidinium, sulfonium, phosphonium or ammonium cations, substituted by at least one lipophilic carbon side chain comprising at least 10 carbon atoms.

According to another embodiment, the invention relates to a process, such as here above defined, wherein the ionic liquid anionic head is chosen among $PF_6^-$, bis(trifluoromethylsulfonyl)imide ($NTf_2^-$), $BF_4^-$, tris(pentafluoroethyl)trifluorophosphate (FAP), alkylsulfates with an alkyl chain from 1 to 20 carbons, alkylsulfonates with an alkyl chain from 1 to 20 carbons, $Cl^-$, $I^-$, $Br^-$, or dialkylphosphates with alkyl chains from 1 to 20 carbons, preferably chosen among $NTf_2^-$, FAP, $PF_6^-$, alkylsulfates According to an advantageous embodiment, the invention relates to a process, such as here above defined, wherein the ionic liquid is chosen among 1-methyl-3-octadecylimidazolium bis(trifluoromethylsulfonyl)imide, 1-hexadecyl-3-methylimidazolium bis(trifluoromethyl)sulfonylimide, trimethyloctadecylammonium bis(trifluoromethyl)sulfonylimide.

According to another advantageous embodiment, the invention relates to a process, such as here above defined, wherein the enzyme is a lipase or an esterase, preferably a lipase chosen among the group consisting of *Candida antartica, Candida cylindracea, Candida rugosa, Pseudomonas cepacia, Mucor miehei, Mucor javaicus, Aspergillus niger*, swine pancreas, *Aspergillus subtilis, Bacillus subtilis, Aspergillus orayze, Rhyzopus oryzae, Yarrowia lypolitica, Chromobacterium visocosum, Thermus lanuginose*, pig liver, particularly a lipase B from *Candida antartica*.

According to an advantageous embodiment, the invention relates to a process, such as here above defined, wherein the substrate is chosen among animal fats, sunflower seed oil, soybean oil, palm oil, coconut oil, lin seed oil, rape seed oil, corn oil, cotton seed oil, ground nut oil, canola oil, olive oil, castor oil, jatropha oil, waste edible and non-edible fats and oils, and mixture thereof.

According to another embodiment, the invention relates to a process, such as here above defined, wherein the substrate is an association of at least two different substrates.

According to another advantageous embodiment, the invention relates to a process, such as here above defined, wherein the substrate contains triglycerides, diglycerides, monoglycerides, phospholipids, and mixture thereof.

According to an advantageous embodiment, the invention relates to a process, such as here above defined, wherein the substrate contains in volume at least 30%, in particular 50%, preferably more than 70% of triglycerides.

According to another embodiment, the invention relates to a process, such as here above defined, wherein the substrate contains in volume a water content lower than 10% of water, in particular 2% of water, preferably 0.5% of water.

According to an advantageous embodiment, the invention relates to a process, such as here above defined, wherein the alcohol is selected from the group consisting of alcohols having from 1 to 4 carbon atoms, in particular methanol, ethanol, propanol, butanol, isomer thereof, and mixture thereof, particularly methanol.

According to another embodiment, the invention relates to a process, such as here above defined, wherein the ionic liquid is liquid at the temperature at which the esterification and/or transesterification process is performed,
the ionic liquid is miscible with the substrates,
the ionic liquid is miscible with said alcohol, and
the ionic liquid is miscible with a mixture of the substrate and said alcohol.

According to an advantageous embodiment, the invention relates to a process, such as here above defined, wherein the ionic liquid is immiscible with glycerol formed during the esterification and/or transesterification reaction of the substrate with at least one alcohol, and the ionic liquid is immiscible with fatty acid alkyl esters.

According to an advantageous embodiment, the invention relates to a process, such as here above defined, for the esterification and/or transesterification of the substrate into fatty acid alkyl esters comprising:
an initialization step, consisting in
bringing together at least one substrate, methanol, and NOVOZYME 435 in 1-methyl-3-octadecylimidazolium bis(trifluoromethylsulfonyl)imide, said substrate, methanol, and 1-methyl-3-octadecylimidazolium bis(trifluoromethylsulfonyl)imide forming a single homogeneous liquid phase, stir the reaction at 60° C. for 24 hours, and
a recovery step, consisting in
decanting:
the phase consisting substantially of the fatty acid alkyl esters formed in the esterification and/or transesterification reaction, and
the phase consisting substantially of the glycerol formed in the esterification and/or transesterification reaction, and
a restoration step, consisting in
recovering and purifying (under vacuum) the combination of 1-methyl-3-octadecylimidazolium bis(trifluoromethylsulfonyl)imide and novozyme Novozyme 435, to obtain a purified combination of 1-methyl-3-octadecylimidazolium bis(trifluoromethylsulfonyl)imide and NOVOZYME 435.

Novozyme 435 is a trademark designating a lipase (lipase B) from *Candida antartica* (Novosym® 435, Novo-Nordisk, Denmark)

According to another embodiment, the invention relates to a process, such as here above defined, for the esterification and/or transesterification of the substrate into fatty acid alkyl esters comprising:
a reaction step, consisting in
bringing together at least one substrate, methanol, in a combination of 1-methyl-3-octadecylimidazolium bis(trifluoromethylsulfonyl)imide and NOVOZYME 435, said substrate, methanol, and 1-methyl-3-octadecylimidazolium bis(trifluoromethylsulfonyl)imide forming a single homogeneous liquid phase, stir the reaction at 60° C. for 24 hours, and
a recovery step, consisting in
decanting:
the phase consisting substantially of the fatty acid alkyl esters formed in the esterification and/or transesterification reaction, and
the phase consisting substantially of the glycerol formed in the esterification and/or transesterification reaction, and a restoration step, consisting in
recovering and purifying (under vacuum) the combination of 1-methyl-3-octadecylimidazolium bis(trifluoromethylsulfonyl)imide and NOVOZYME 435, to obtain a purified combination of 1-methyl-3-octadecylimidazolium bis(trifluoromethylsulfonyl)imide and Novozyme 435.
with the three said steps defined above forming a cycle.

The invention relates to a reaction mixture comprising an enzyme and a single homogeneous liquid phase at the temperature, at which the process is performed, containing,
at least an ionic liquid,
at least a substrate, said substrate consisting of oils, fats, fatty acids, or a mixture thereof, and
at least an alcohol.

The four components of the reaction are the substrate, the alcohol, the enzyme and the ionic liquid. The reaction mixture is obtained after bringing together the four components, as the esterification and/or transesterification of substrate and alcohol into fatty acid alkyl esters starts.

The invention relates to a reaction mixture comprising an enzyme and a single homogeneous liquid phase at room temperature, containing,
at least an ionic liquid,
at least a substrate, said substrate consisting of oils, fats, fatty acids, or a mixture thereof, and
at least an alcohol.

The four components of the reaction are the substrate, the alcohol, the enzyme and the ionic liquid. The reaction mixture is obtained after bringing together the four components, as the esterification and/or transesterification of substrate and alcohol into fatty acid alkyl esters starts.

According to another embodiment, the invention relates to a reaction mixture, such as here above defined, wherein the alcohol and the substrate (i.e. triacylglycerides) have a molar ratio from about 1:1 to about 10:1, preferably from about 3:1 to about 6:1.

Considering the stoichiometric ratio between the substrate and the alcohol, three cases are possible:
the substrate is composed of triglycerides only, then the stoichiometric molar ratio to reach full conversion is 3:1,
the substrate is composed of fatty acids and/or monoglycerides only, then the stoichiometric molar ratio is 1:1,
the substrate is composed of a mixture of glycerides and fatty acids, then the stoichiometric molar ratio is ranging from 1:1 to 3:1.

In other words, the molar ratio between the substrate and the alcohol can be expressed with respect to the number of the fatty acyl chains born by the substrate. Monoglycerides (monoacylglycerol) and fatty acids have 1 fatty acyl chain, diglycerides (diacylglycerol) have 2 fatty acid chains, and triglycerides (triacylglycerol) have 3 fatty acyl chains.

Taken into account that 1 mole of alcohol reacts with 1 mole of fatty acyl side chain, if the alcohol and the substrates (i.e. triacylglycerols) have a molar ratio lower than 3:1 (in other words less than 1 molar equivalent of alcohol with respect to each mol of fatty acyl chain of the substrate when the substrate is a triacylglycerol), it is certain that whatever the exact composition of the substrate is, the reaction is not complete with respect to the substrate. Furthermore, alcohols are volatile compounds, and in order to provide a good shift of the reaction equilibrium towards full conversion of the substrate into biodiesel, an excess of alcohol with respect to the overall molar fatty acyl chain concentration is recommended. Thus a molar ratio between alcohol and fatty acyl chains of 2:1 is recommended in all cases. However, molar ratio between alcohol and fatty acyl chain higher than 3:1 will reduce the enzyme activity by deactivation phenomena.

As alcohols (i.e. methanol) are not expensive, and can be recycled in the present process, it is advantageous from an industrial point of view to use more molar equivalents of alcohol than the maximum possible stoichiometric molar ratio.

According to an advantageous embodiment, the invention relates to a reaction mixture, such as here above defined, wherein
the enzyme and its support have a weight ratio to the substrate from about 1:1 to about 1:200, preferably 1:10 for a supported enzyme,
or an enzyme to substrate weight ratio from 1:50 to about 1:20000, preferably 1:500 for a non supported enzyme.

The amount of enzyme should be optimized as a function of the observed activity in biodiesel production at the assayed reaction conditions with respect the assayed substrate. The increase in the amount of enzyme always involves a decrease in reaction time and an increase in overall cost, and vice versa.

Two different types of enzymes can be used according to the present invention: supported or non supported enzymes.

When supported enzymes are used, the enzyme to substrate ratio should take into account the molar weight of the enzymes as well as the molar weight of the particles supporting the enzymes, and the amount of enzymes present on each particle. This information is provided by the supported enzymes manufacturer, and thus the calculation of the ratio is straightforward to the man skilled in the art.

Non supported enzymes do not have support particles and only their molecular weight is taken into account for the calculation of the enzyme to substrate ratio.

According to another advantageous embodiment, the invention relates to a reaction mixture, such as here above defined, wherein the ionic liquid and the substrate have a volume ratio from about 20:1 to about 1:20, preferably 3:1.

The IL:substrate volume ratio is dependent on the phase behaviour of the system, and obviously it is recommended to use the lowest amount of IL that dissolves the highest amount of triglycerides while maintaining a single homogeneous liquid phase.

According to an advantageous embodiment, the invention relates to a reaction mixture, such as here above defined, wherein the ionic liquid and the alcohol have a volume ratio from about 20:1 to about 1:1, preferably 8:1.

According to an advantageous embodiment, the invention relates to a reaction mixture, such as here above defined, wherein the ratio between the volume of the ionic liquid and the sum of the volumes of the alcohol and the substrate is from about 90/10 to about 10/90, preferably from about 70/30 to about 50/50, preferably 66/33.

Ionic liquids are expensive compounds, thus it is economically advantageous to use the minimum amount of ionic liquid in order to solubilise the maximum amount of substrate and alcohol while preserving the single homogeneous phase.

According to another embodiment, the invention relates to a reaction mixture, such as here above defined, comprising water in an amount of from about 0% to about 5%, in particular from about 0% to about 2%, preferably from about 0% to about 0.5%, of the sum of the ionic liquid, the substrate and the alcohol volumes.

Water may disturb the reaction as it can have deleterious effects on the enzymes, and can reduce the enzyme activity. Thus, the water content in the reaction mixture should be as low as possible.

The invention relates to a reaction mixture consisting substantially of 3 phases:

a first phase consisting substantially of at least one ionic liquid, and at least one enzyme,
a second phase consisting substantially of glycerol,
a third phase consisting substantially of fatty acid alkyl esters,
wherein said ionic liquid is liquid at the temperature at which the process is performed.

The invention relates to a reaction mixture consisting substantially of 3 phases:
a first phase consisting substantially of at least one ionic liquid, at least one enzyme, and at least one alcohol,
a second phase consisting substantially of glycerol and at least one alcohol,
a third phase consisting substantially of fatty acid alkyl esters,
wherein said ionic liquid is liquid at the temperature at which the process is performed.

The invention relates to a reaction mixture consisting substantially of 3 phases:
a first phase consisting substantially of at least one ionic liquid, at least one enzyme, and at least one substrate, said substrate consisting of oils, fats, fatty acids, or a mixture thereof,
a second phase consisting substantially of glycerol,
a third phase consisting substantially of fatty acid alkyl esters,
wherein said ionic liquid is liquid at the temperature at which the process is performed.

The invention relates to a reaction mixture consisting substantially of 3 phases:
a first phase consisting substantially of at least one ionic liquid, at least one enzyme, at least one substrate, said substrate consisting of oils, fats, fatty acids, or a mixture thereof, and at least one alcohol,
a second phase consisting substantially of glycerol and at least one alcohol.
a third phase consisting substantially of fatty acid alkyl esters,
wherein said ionic liquid is liquid at the temperature at which the process is performed.

According to an advantageous embodiment, the invention relates to a reaction mixture consisting substantially of 3 phases:
a first phase consisting substantially of at least one ionic liquid, at least one enzyme, at least one substrate, at least one alcohol, at least one fatty acid, at least one monoglyceride, at least one diglyceride and at least one triglyceride,
a second phase consisting substantially of glycerol, at least one alcohol, at least one fatty acid, at least one monoglyceride and at least one diglyceride,
a third phase consisting substantially of fatty acid alkyl esters, at least one diglyceride and at least one triglyceride.

The ionic liquid, the glycerol and the fatty acid alkyl esters are immiscible and form three phases.

During the reaction process, intermediate products such as diglycerides, monoglycerides and possibly fatty acids are formed. These intermediate products may be miscible in two or more of the three immiscible phases (ionic liquid, glycerol and fatty acid alkyl esters) and induce a modification in the partition coefficients.

Thus, the solubility of the ionic liquid, the glycerol and the fatty acid alkyl esters towards each other may be modified, and the three immiscible phases described above may not be clearly separated while the reaction proceeds.

According to another embodiment, the invention relates to a reaction mixture, such as here above defined, free from inorganic acid and base.

It is advantageous not to use acid or base, because aqueous extraction will be required to remove the traces of acid or base that will be present in the biodiesel obtained, and further drying of the biodiesel will be necessary to remove the traces of water. Industrial process would be longer and more costly.

Furthermore, acids and bases are deleterious for the engines. Thus traces of acids or base in the biodiesel should be avoided.

Inorganic acid and base are defined as acids and bases which are not organic. Organic acids and bases are carbon containing compounds.

According to an advantageous embodiment, the invention relates to a reaction mixture, such as here above defined, free from salt and co-solvent.

The expression "salt" means any kind of inorganic salt, and non carbonaceous salt.

The expression "co-solvent" means a solvent which is not the main solvent used in the reaction in volume proportion, but
contribute to the solubility of all, or a part, of the following components: substrate, the alcohol, the enzyme in the ionic liquid, and/or
contribute to reduce the melting temperature of the ionic liquid.

According to another advantageous embodiment, the invention relates to a reaction mixture, such as here above defined, containing an alcohol and a co-solvent, said co-solvent being able to react with the substrate to produce fatty acid alkyl esters.

The co-solvent, i.e. t-butanol, may be able to react with the substrate to form a fatty acid alkyl ester, but the reactivity of the co-solvent is inferior to the reactivity of the alcohol used as a reaction component in the esterification and/or transesterification process.

The proportion of the amount of reacting co-solvent is minute compared to the total amount of the alcohol which has been defined as a component of the reaction.

According to another embodiment, the invention relates to a reaction mixture, such as here above defined, containing an alcohol and a co-solvent, said co-solvent being not able to react with the substrate to produce fatty acid alkyl esters.

The co-solvent (i.e. acetonitrile) is not able to react with the substrate to form fatty acid alkyl ester. The co-solvent is added to the ionic liquid in order to modify the melting temperature of the ionic liquid, or to increase the solubility of one, or several, reactants within the ionic liquid.

DESCRIPTION OF THE FIGURES

Figures

Figure 1:
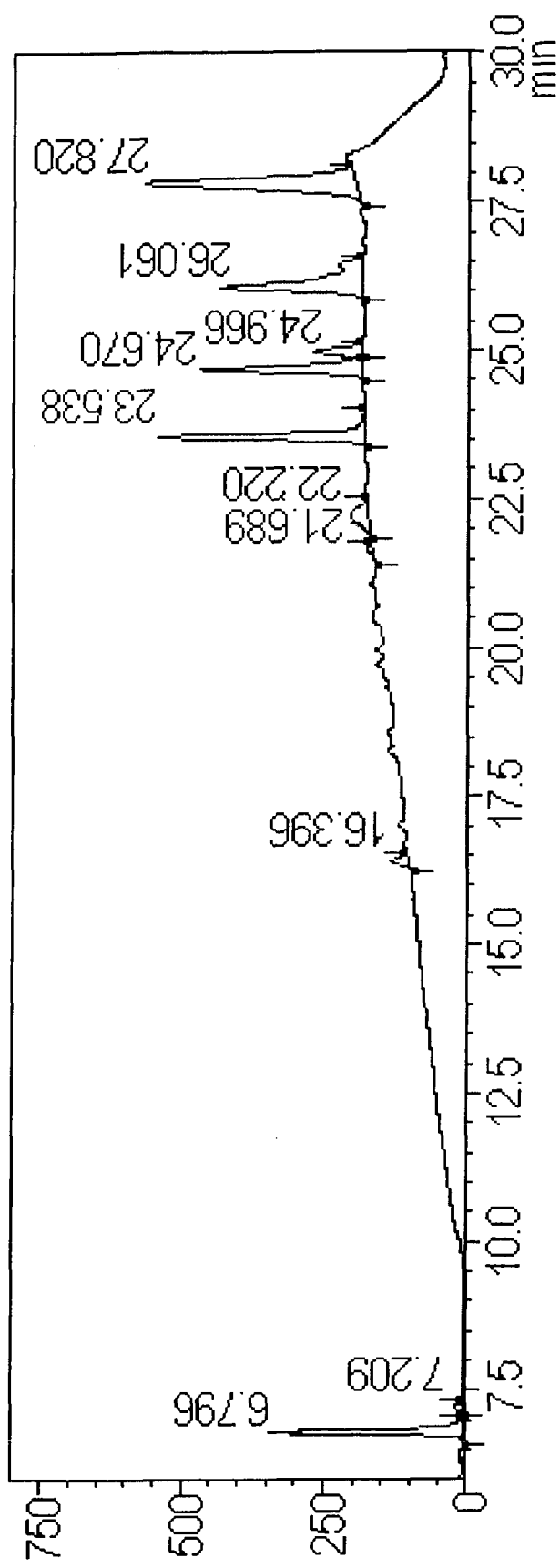
FIG. 1 is a HPLC chromatogram, obtained from example 1.2 at the beginning of the reaction (t=0). Elution parameters and column characteristics are as described in example 1.2. Retention time is indicated next to the peak. Peak at 6.8 min is the internal standard (Ethyl decanoate). Triglyceride peaks are trilinolein 23.5 min and triolein 27.8 min. No fatty acid alky ester peak can be seen.
Figure 2:
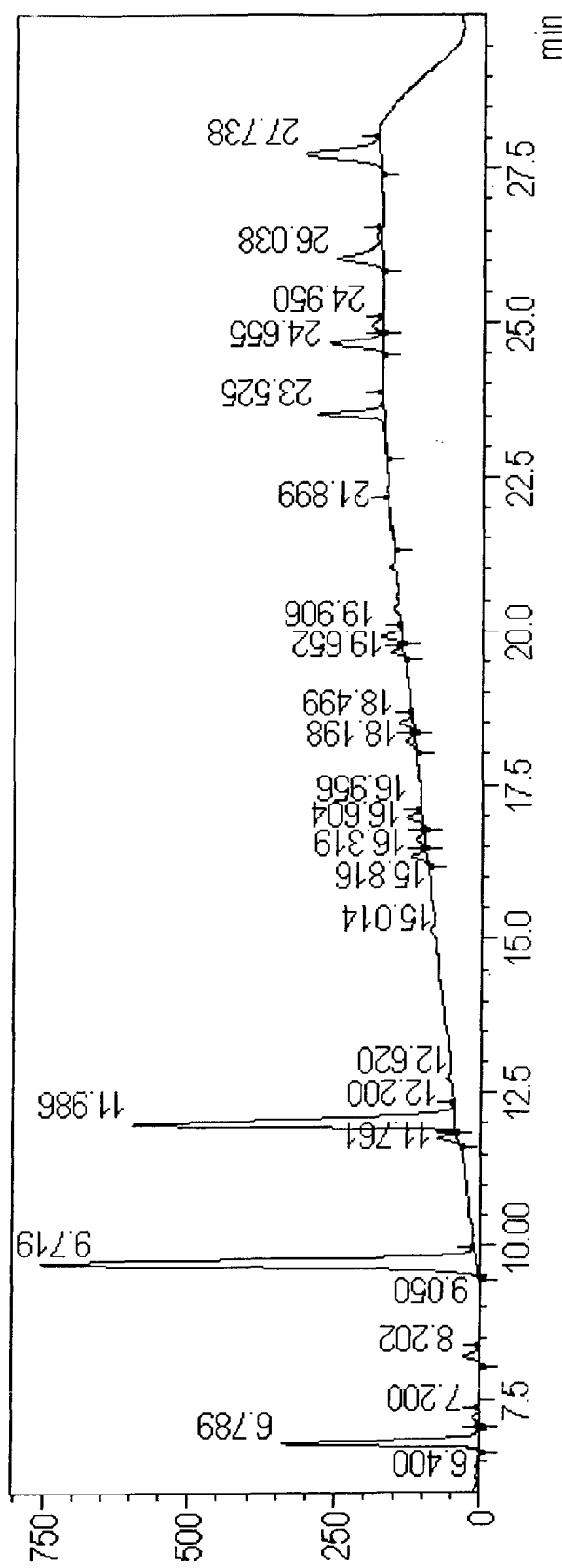
FIG. 2 is a HPLC chromatogram, obtained from example 1.2 after 2 hours of reaction (t=2 h). Elution parameters and column characteristics are as described in example 1.2. Retention time is indicated next to the peak. Peak at 6.8 min is the internal standard (Ethyl decanoate). Several new peaks appeared. Triglyceride (trilinolein 23.5 min and triolein 27.8 min) intensities have decreased compared to the reference, indicating that triglycerides have been consumed. Two intense new peaks of fatty acid alky esters appear at 9.7 min (Methyl linoleate) and 12.0 min (Methyl oleate).
Figure 3:
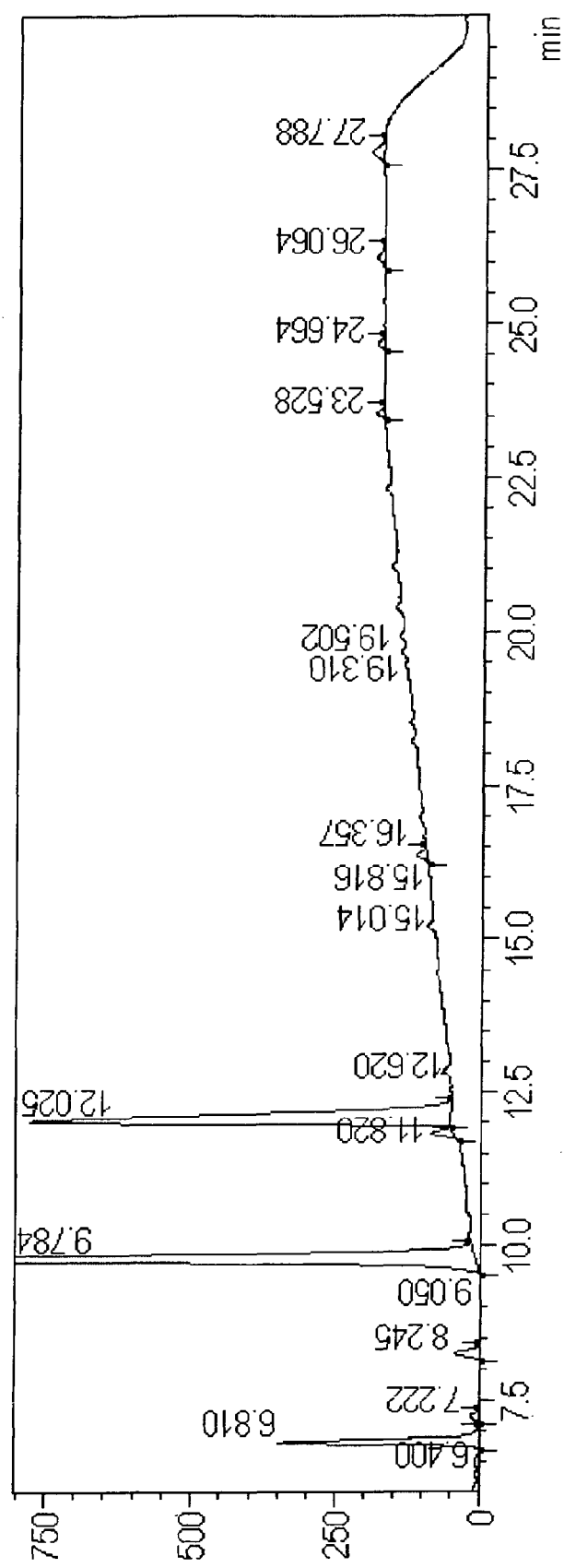

FIG. 3 is a HPLC chromatogram, obtained from example 1.2 after 6 hours of reaction (t=6 h). Elution parameters and column characteristics are as described in example 1.2. Retention time is indicated next to the peak. Peak at 6.8 min is the internal standard (Ethyl decanoate). Triglyceride peaks (trilinolein 23.5 min and triolein 27.8 min) almost disappeared, indicating that almost all triglycerides have been consumed. The two intense peaks of fatty acid alky esters (9.7 min. Methyl linoleate, and 12.0 min Methyl oleate) remain.

Figure 4:
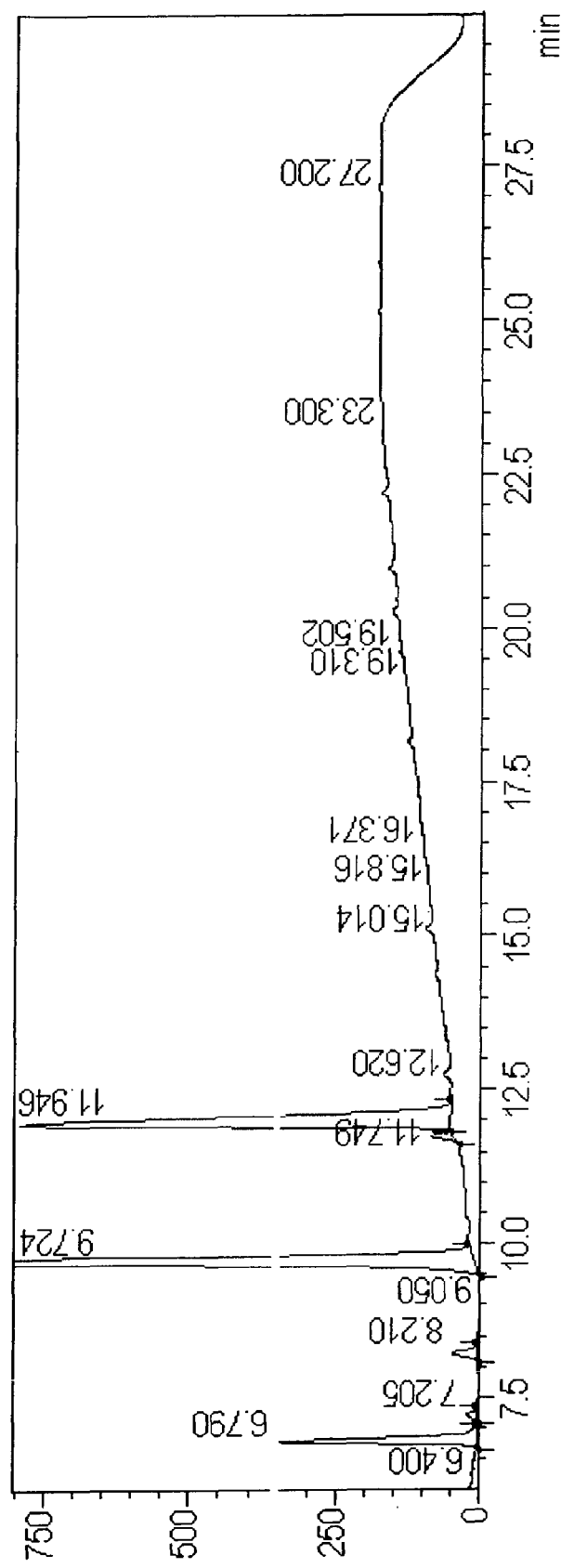

FIG. 4 is a HPLC chromatogram, obtained from example 1.2 after 24 hours of reaction (t=24 h). Elution parameters and column characteristics are as described in example 1.2. Retention time is indicated next to the peak. Peak at 6.8 min is the internal standard (Ethyl decanoate). Triglyceride peaks (trilinolein 23.5 min and triolein 27.8 min) disappeared, indicating that all triglycerides have been consumed. Except for the internal reference, only the two intense peaks of the fatty acid alky esters (9.7 min. Methyl linoleate, and 12.0 min Methyl oleate) remain. The reaction is complete.

Figure 5:
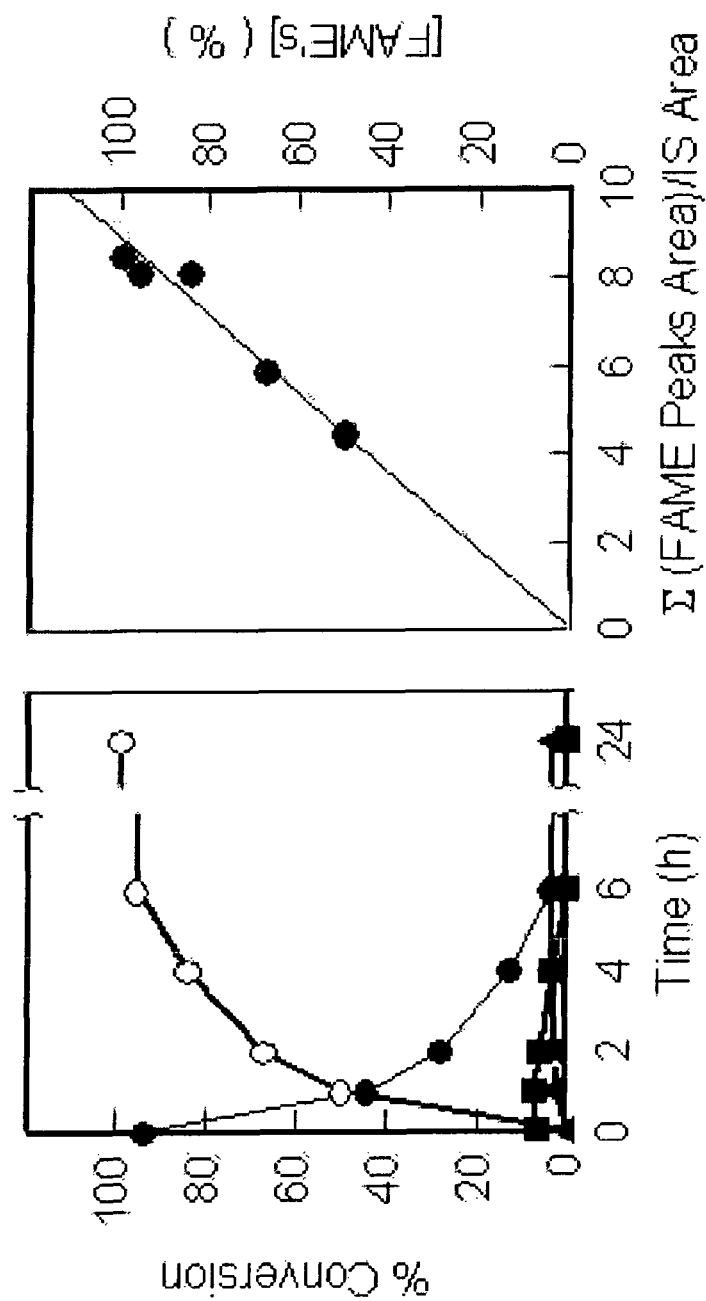

FIG. 5 represents two diagrams.

the left part represents the percentage of each kind of compounds present in the reaction, namely triglycerides (TG) (black circle), diglycerides (DG) (black square), monoglycerides (MG) (black triangle) and fatty acid alky esters (FAME) (hollow circle), in function of the reaction time.

the right part represents the sum of the FAME peak area normalised by the internal standard peak area, plotted against the FAME concentration percentage. It shows the good agreement between the normalised area of FAME compounds and their concentration in percentage.

These data are as collected in example 1.2. The quantities are determined using a calculation protocol based on the integration area of HPLC peak (see FIGS. 1 to 4), and the assumption that each MG compound generates one FAME, each DG compound generates two FAME, and each TG compound generates three FAME.

By this procedure, the extension of the biocatalytic step according to the detection time can be clearly observed, enabling to detect when the full conversion of oil to biodiesel has occurred.

FIGS. 6a, 6b, 6c and 6d are four pictures.

Each of these four pictures represents a screw capped test tube (1.5 mL) half filled with a mixture consisting in: an ionic liquid ([$C_{14}$MIM][NTf$_2$], 0.672 g), triolein (222 µL, 0.202 g) and methanol (48 µL, 0.038 g).

The four pictures show a monophasic homogeneous liquid mixture.

Each picture was taken at a different temperature.

Figure 6A:
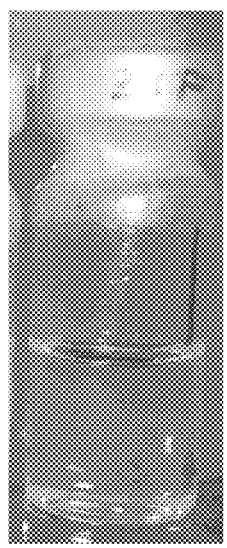
Figure 6B:
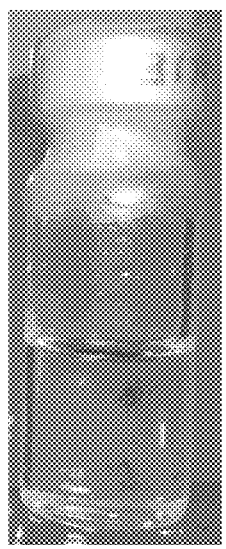
Figure 6C:
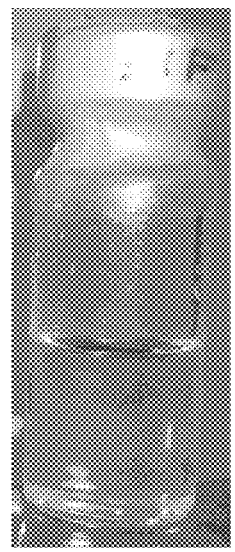
Figure 6D:
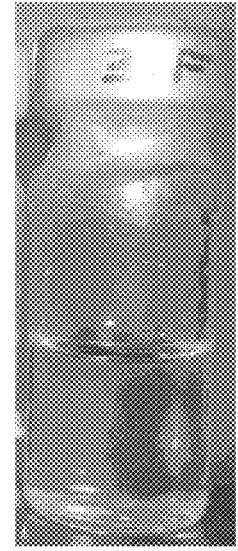

FIG. 6a: picture was taken at 30° C.,
FIG. 6b: picture was taken at 40° C.,
FIG. 6c: picture was taken at 50° C.,
FIG. 6d: picture was taken at 60° C.

FIGS. 7a, 7b, 7c and 7d are four pictures.

Each of these four pictures represents a screw capped test tube (1.5 mL) half filled with a mixture consisting in: an ionic liquid ([$C_{16}$MIM][NTf$_2$], 0.672 g), triolein (222 µL, 0.202 g) and methanol (48 µL, 0.038 g).

The four pictures show a monophasic homogeneous liquid mixture.

Each picture was taken at a different temperature.

Figure 7A:
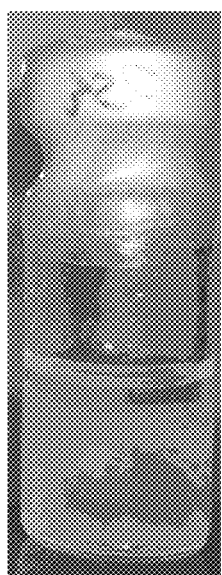
Figure 7B:
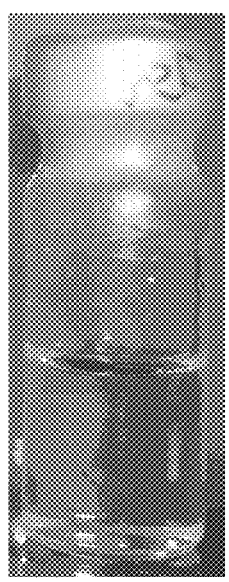
Figure 7C:
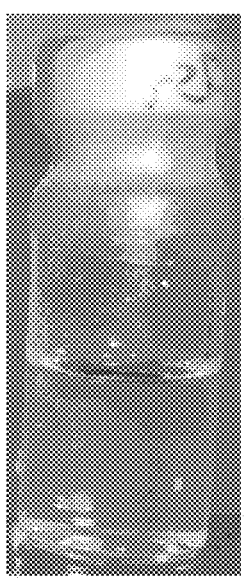
Figure 7D:
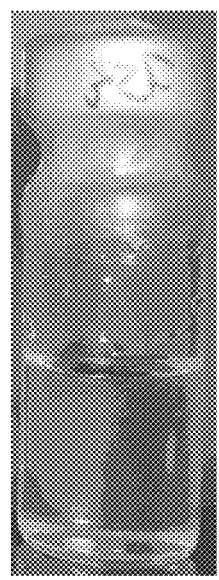

FIG. 7a: picture was taken at 30° C.,
FIG. 7b: picture was taken at 40° C.,
FIG. 7c: picture was taken at 50° C.,
FIG. 7d: picture was taken at 60° C.

FIGS. 8a, 8b, 8c, 8d and 8e are five pictures.

Each of these five pictures represents four screw capped test tubes (1.5 mL) half filled with a mixture that vary for each tube.

First tube form the left: an ionic liquid ([$C_{18}$MIM][NTf$_2$], 0.295 g), triolein (595 µL, 0.541 g) and methanol (150 µL, 0.118 g).

Second tube from the left: an ionic liquid ([$C_{18}$MIM][NTf$_2$], 0.448 g), triolein (444 µL, 0.404 g) and methanol (112 µL, 0.088 g).

Third tube from the left: an ionic liquid ([$C_{18}$MIM][NTf$_2$], 0.590 g), triolein (302 µL, 0.275 g) and methanol (76 µL, 0.06 g).

Fourth tube from the left: an ionic liquid ([$C_{18}$MIM][NTf$_2$], 0.672 g), triolein (222 µL, 0.202 g) and methanol (48 µL, 0.038 g).

Each picture was taken at a different temperature.

Figure 8A:
Figure 8B:
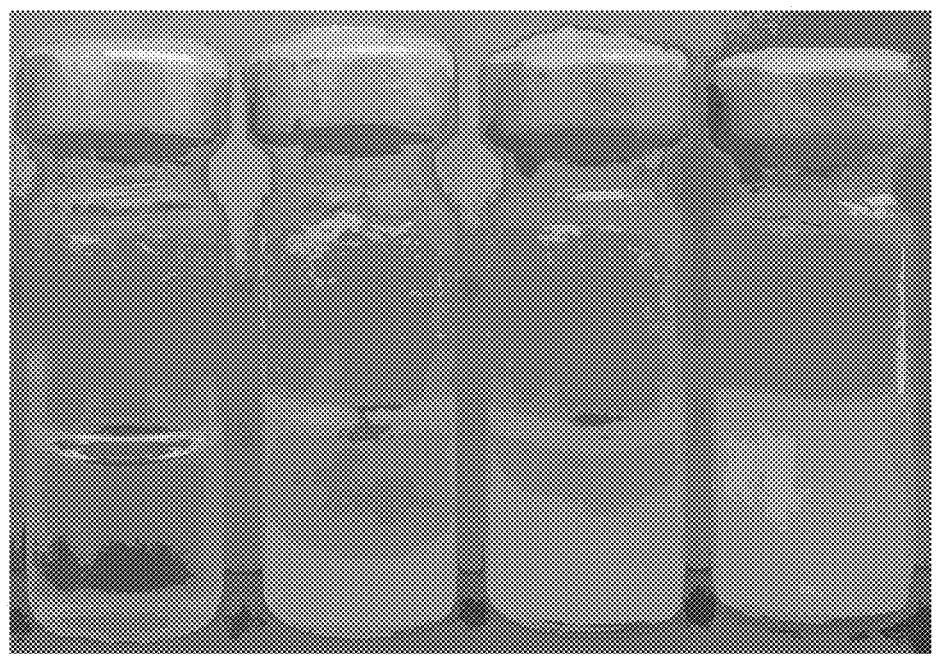
Figure 8C:
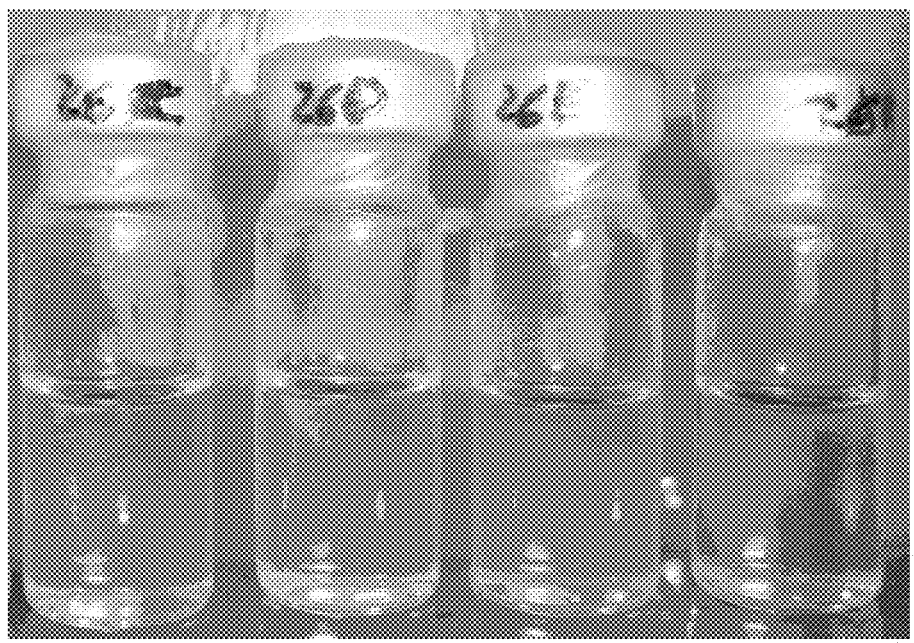
Figure 8D:
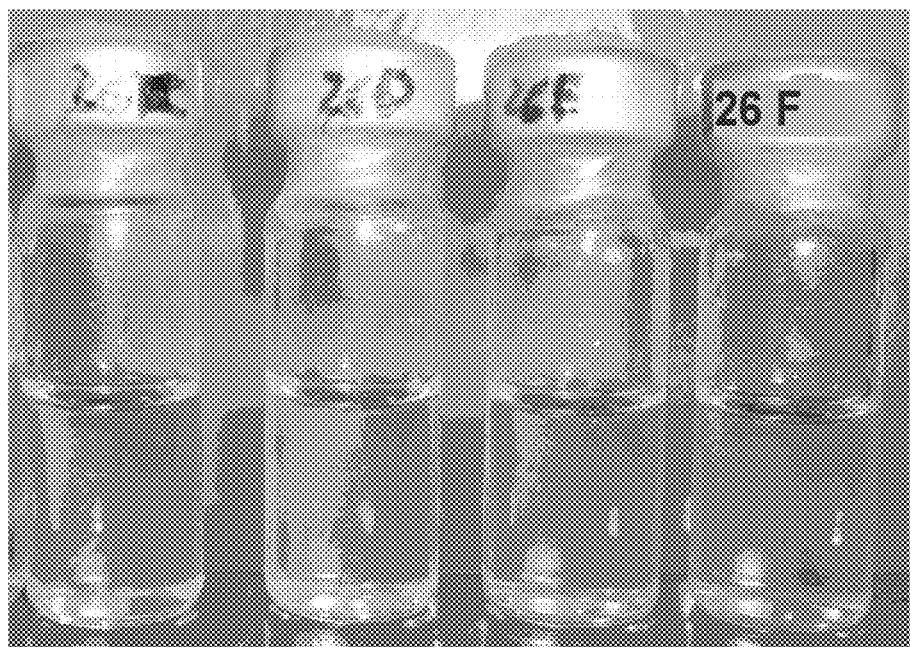
Figure 8E:
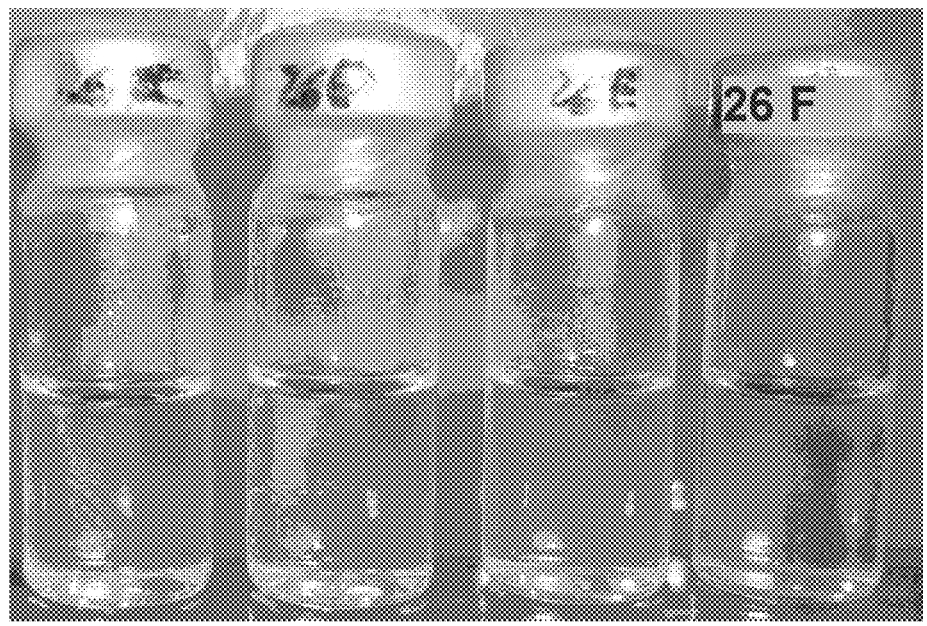

FIG. 8a: picture was taken at 30° C., the four tubes contain a biphasic solid-liquid mixtures, FIG. 8b: picture was taken at 40° C., the first tube from the left contains a monophasic homogeneous liquid mixture, the three other tubes contain biphasic solid-liquid mixtures, FIG. 8c: picture was taken at 50° C., the four tubes contain monophasic homogeneous liquid mixtures, FIG. 8d: picture was taken at 60° C., the four tubes contain monophasic homogeneous liquid mixtures, FIG. 8e: picture was taken at 70° C., the four tubes contain monophasic homogeneous liquid mixtures.

FIGS. 9a, 9b, 9c and 9d are four pictures.

Each of these four pictures represents a screw capped test tube (1.5 mL) half filled with a mixture consisting in: an ionic liquid ([$C_{18}$MIM][PF$_6$], 0.448 g), triolein (444 µL, 0.404 g) and methanol (112 µL, 0.088 g).

Each picture was taken at a different temperature.

Figure 9A:
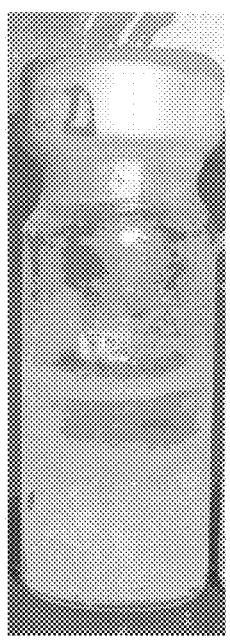
Figure 9B:
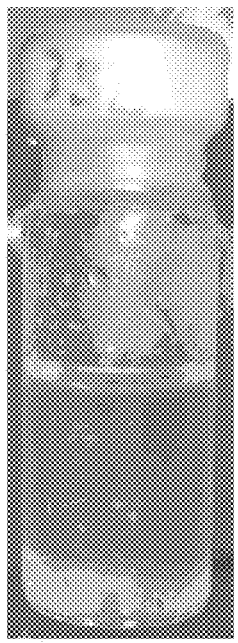
Figure 9C:
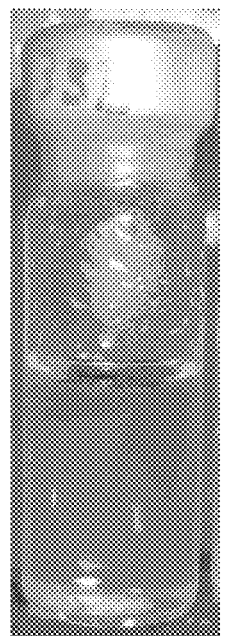
Figure 9D:
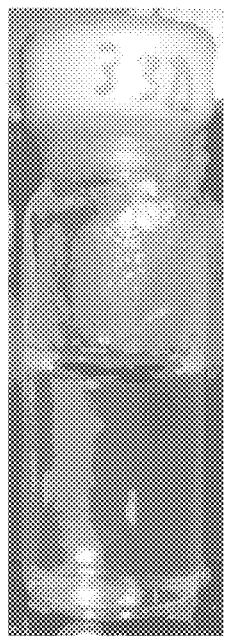

FIG. 9a: picture was taken at 60° C., the tube contains a biphasic solid-liquid mixture, FIG. 9b: picture was taken at 70° C., the tube contains a biphasic solid-liquid mixture, FIG. 9c: picture was taken at 80° C., the tube contains a monophasic homogeneous liquid mixture, FIG. 9d: picture was taken at 90° C., the tube contains a monophasic homogeneous liquid mixture.

Figure 10A:
Figure 10B:
Figure 10C:
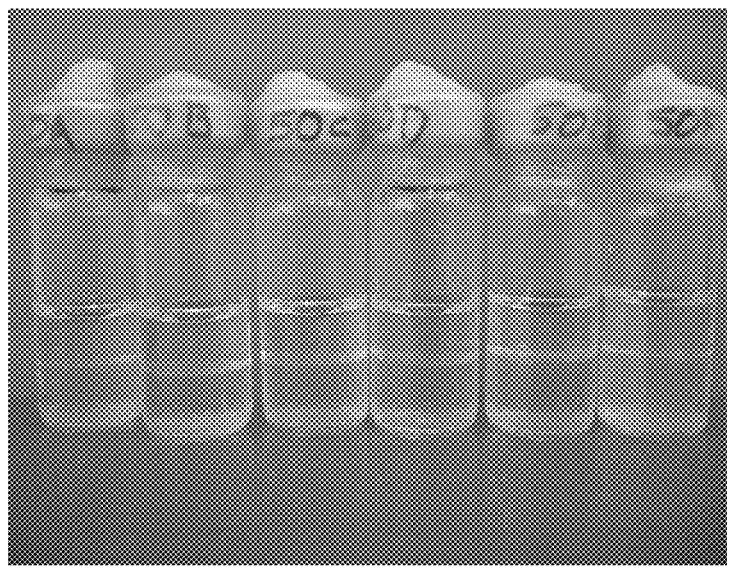

FIGS. 10a, 10b and 10c are three pictures.

Each of these three pictures represents six screw capped test tubes (1.5 mL) half filled with a mixture consisting in an ionic liquid ([OMIM][NTf$_2$], 375 µL), triolein (375 µL) and methanol.

The volume of methanol varies for each tube:
First tube from the left: 32 µL of methanol,
Second tube from the left: 47 µL of methanol,
Third tube from the left: 64 µL of methanol,
Fourth tube from the left: 94 µL of methanol,
Fifth tube from the left: 128 µL of methanol,
Sixth tube from the left: 160 µL of methanol.

Each picture was taken at a different temperature.

FIG. 10a: picture was taken at 40° C., the six tubes contain a biphasic liquid-liquid mixtures, FIG. 10b: picture was taken at 50° C., the six tubes contain a biphasic liquid-liquid mixtures, FIG. 10c: picture was taken at 60° C., the six tubes contain a biphasic liquid-liquid mixtures.

Figure 11:

FIG. 11 is a picture.

The picture represents four screw capped test tubes (1.5 mL) half filled with a mixture consisting in an ionic liquid (250 mg) (said ionic liquid is different for each tube) and glycerol (600 mg). The picture was taken at room temperature (22° C.).

The ionic liquid varies for each tube:
First tube from the left: $[C_{12}MIM][BF_4]$,
Second tube from the left: $[C_{14}MIM][BF_4]$,
Third tube from the left: $[C_{16}MIM][BF_4]$,
Fourth tube from the left: $[C_{18}MIM][BF_4]$.
The four tubes contain a biphasic mixture.

Figure 12:
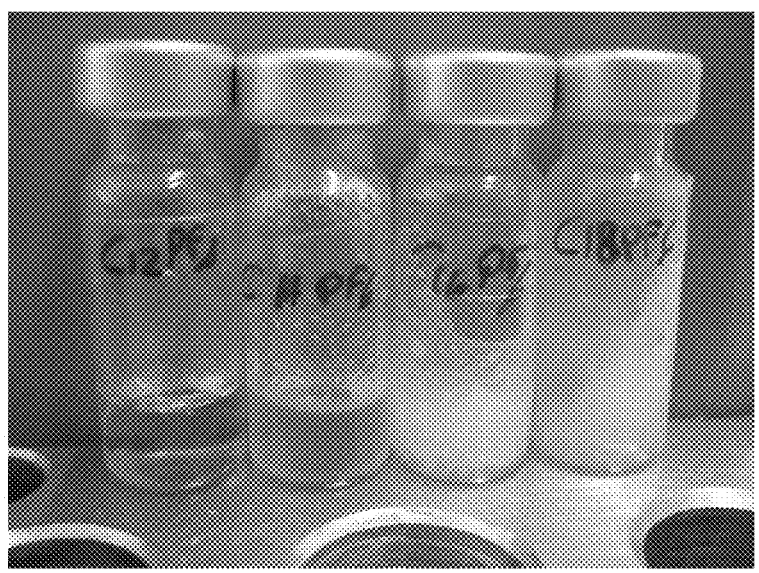

FIG. 12 is a picture.

The picture represents four screw capped test tubes (1.5 mL) half filled with a mixture consisting in an ionic liquid (250 mg) (said ionic liquid is different for each tube) and glycerol (600 mg). The picture was taken at room temperature (22° C.).

The ionic liquid varies for each tube:
First tube from the left: $[C_{12}MIM][PF_6]$,
Second tube from the left: $[C_{14}MIM][PF_6]$,
Third tube from the left: $[C_{16}MIM][PF_6]$,
Fourth tube from the left: $[C_{18}MIM][PF_6]$.
The four tubes contain a biphasic mixture.

Figure 13:

FIG. 13 is a picture.

The picture represents four screw capped test tubes (1.5 mL) half filled with a mixture consisting in an ionic liquid (250 mg) (said ionic liquid is different for each tube) and glycerol (600 mg). The picture was taken at room temperature (22° C.).

The ionic liquid varies for each tube:
First tube from the left: $[C_{12}MIM][NTf_2]$,
Second tube from the left: $[C_{14}MIM][NTf_2]$,
Third tube from the left: $[C_{16}MIM][NTf_2]$,
Fourth tube from the left: $[C_{18}MIM][NTf_2]$.
The four tubes contain a biphasic mixture.

Figure 14:

FIG. 14 is a picture.

The picture represents four screw capped test tubes (1.5 mL) half filled with a mixture consisting in an ionic liquid (250 mg) (said ionic liquid is different for each tube) and methyl oleate (600 mg) (biodiesel). The picture was taken at 30° C.

The ionic liquid varies for each tube:
First tube from the left: $[C_{12}MIM][BF_4]$,
Second tube from the left: $[C_{14}MIM][BF_4]$,
Third tube from the left: $[C_{16}MIM][BF_4]$,
Fourth tube from the left: $[C_{18}MIM][BF_4]$.
The four tubes contain a biphasic mixture.

Figure 15:

FIG. 15 is a picture.

The picture represents four screw capped test tubes (1.5 mL) half filled with a mixture consisting in an ionic liquid (250 mg) (said ionic liquid is different for each tube) and methyl oleate (600 mg) (biodiesel). The picture was taken at 30° C.

The ionic liquid varies for each tube:
First tube from the left: $[C_{12}MIM][PF_6]$,
Second tube from the left: $[C_{14}MIM][PF_6]$,
Third tube from the left: $[C_{16}MIM][PF_6]$,
Fourth tube from the left: $[C_{18}MIM][PF_6]$.
The four tubes contain a biphasic mixture.

Figure 16:
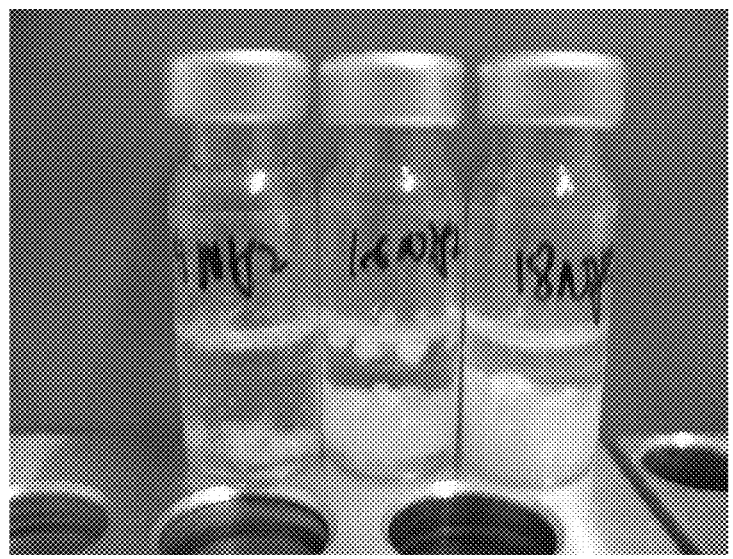

FIG. 16 is a picture.

The picture represents three screw capped test tubes (1.5 mL) half filled with a mixture consisting in an ionic liquid (250 mg) (said ionic liquid is different for each tube) and methyl oleate (600 mg) (biodiesel). The picture was taken at 30° C.

The ionic liquid varies for each tube:
First tube from the left: $[C_{14}MIM][NTf_2]$,
Second tube from the left: $[C_{16}MIM][NTf_2]$,
Third tube from the left: $[C_{18}MIM][NTf_2]$.
The three tubes contain a biphasic mixture.

Figure 17:

FIG. 17 is a picture.

The picture represents a graduated pipette filled by a mixture consisting in an ionic liquid ($[C_{18}MIM][NTf_2]$, 400 mg), methyl oleate (800 mg) and glycerol (800 mg). The picture was taken at room temperature (22° C.).

The picture shows three phases.
top: liquid methyl oleate,
middle: solid $[C_{18}MIM][NTf_2]$,
bottom: liquid glycerol.

Figure 18:

FIG. 18 is a picture.

The picture represents four screw capped test tubes (1.5 mL) half filled with a mixture consisting in an ionic liquid (2.50 g) (said ionic liquid is different for each tube), methyl oleate (500 mg) (biodiesel) and glycerol (500 mg). The picture was taken at room temperature (22° C.).

The ionic liquid varies for each tube:
First tube from the left: $[C_{12}MIM][BF_4]$,
Second tube from the left: $[C_{14}MIM][BF_4]$,
Third tube from the left: $[C_{16}MIM][BF_4]$,
Fourth tube from the left: $[C_{18}MIM][BF_4]$.
The four tubes contain a triphasic mixture (liquid methyl oleate on top, solid ionic liquid in the middle, liquid glycerol at the bottom).

Figure 19:

FIG. 19 is a picture.

The picture represents four screw capped test tubes (1.5 mL) half filled with a mixture consisting in an ionic liquid (2.50 g) (said ionic liquid is different for each tube), methyl oleate (500 mg) (biodiesel) and glycerol (500 mg). The picture was taken at room temperature (22° C.).

The ionic liquid varies for each tube:
First tube from the left: $[C_{12}MIM][PF_6]$,
Second tube from the left: $[C_{14}MIM][PF_6]$,
Third tube from the left: $[C_{16}MIM][PF_6]$,
Fourth tube from the left: $[C_{18}MIM][PF_6]$.
The four tubes contain a triphasic mixture (liquid methyl oleate on top, solid ionic liquid in the middle, liquid glycerol at the bottom).

Figure 20:

FIG. 20 is a picture.

The picture represents three screw capped test tubes (1.5 mL) half filled with a mixture consisting in an ionic liquid (2.5 g) (said ionic liquid is different for each tube), methyl oleate (500 mg) (biodiesel) and glycerol (500 mg). The picture was taken at room temperature (22° C.).

The ionic liquid varies for each tube:
First tube from the left: $[C_{14}MIM][NTf_2]$,
Second tube from the left: $[C_{16}MIM][NTf_2]$,
Third tube from the left: $[C_{18}MIM][NTf_2]$.
The first tube from the left contains a triphasic mixture (liquid methyl oleate on top, liquid ionic liquid in the middle, liquid glycerol at the bottom).

The second and third tubes from the left contain a triphasic mixture (liquid methyl oleate on top, solid ionic liquid in the middle, liquid glycerol at the bottom).

I STANDARD REACTION CONDITIONS AND PROCEDURES

The ionic liquids used in the present invention are neutral (pH 6.8 to 7.4). pH of the ionic liquid is checked with pH-paper (i.e. Neutralit® pH 5.5-9.0, Merck, Ref 109560; or Acilit® pH 0.5-13.0, Merck Ref. 109565). In order to measure the pH of the ionic liquid there ought to be some traces of water in the ionic liquid. If the ionic liquid is dry, then an aliquot of said ionic liquid is mixed in water and the pH of the aqueous solution is checked.

The procedure for the biocatalytic production of biodiesel in ionic liquid (IL) occurs in two different steps, as follows:

1. Biotacalytic Step

The reaction occurs in any of the conditions described previously, as follows: concentration ratio between oil and methanol, volume ratio between IL and oil, weight ratio between oil and enzyme, at a temperature comprised between 40-80° C. The biocatalytic reactor is any vessel equipped with a closing system avoiding evaporation in particular of low molecular weight alcohols. Preferably, both heating and mixing steps are carried out into a thermostatic bath with shaking via a rotating system or an automatically thermostatic oscillating shaker, or any other system suitable for thermostatic mixing.

2. Biodiesel Recovery and IL Recycle Steps

Once the reaction is over, the full reaction mixture can be submitted to different separation techniques such as evaporation by heat and/or under reduced pressure, liquid-liquid extraction, supercritical fluid extraction, distillation, centrifugation, membrane separation, pervaporation, chromatography to separate the different components.

The biodiesel recovery and recycling of reaction system occur in several steps, as follows:

2.1. Enzyme Recovery.

Optionally, the reaction mixture is centrifuged at the lowest temperature that allows the reaction mixture to keep liquid, and then the immobilized enzyme particles are recovered by simple decantation. The immobilized enzyme particles are stored in a dessicator containing silica gel at room temperature until the next catalytic cycle.

2.2. Removal of the Residual Primary Aliphatic Alcohols

The residual primary aliphatic alcohols are removed from the reaction mixture under vacuum at 50-70° C. for 2 to 10 min.

2.3. Elimination of Glycerol.

An equivalent volume of water is added to the resulting reaction mixture, and the biphasic system mixed into a rotator system at 50-70° C. and 100 rpm for 30 min. Then, the aqueous phase containing glycerol is eliminated by simple decantation. This process can be repeated 3 times.

2.4. Biodiesel Recovery.

The resulting reaction mixture is cooled to a temperature comprised between 0 and 15° C., in order to induce the solidification of the IL fraction which is present in the reaction media. The biodiesel can be separated from the solid IL by simple decantation. Then, the remaining IL solid phase can be washed with an organic solvent (non-miscible with the IL) in order to extract any remaining amount of biodiesel. Alternative procedures to extract the remaining biodiesel (i.e. distillation) from the IL can also be applied.

2.5. Drying of the Ionic Liquid.

The remaining IL solid fraction is maintained at a reduced pressure below 1 bar and 80° C. and 100 rpm, for 10 min to 1 hour (as a function of its volume) to eliminate all the remaining molecular solvents (e.g. water, organic solvent, biodiesel, etc). The resulting clean IL is ready to start a new catalytic cycle.

II REACTION SYSTEM

1—Monophasic Homogeneous Initial Reaction Mixture

Example 1

Ionic liquid ($[C_{14}MIM][NTf_2]$, 0.672 g), triolein (0.202 g, 222 µL) and methanol (0.038 g, 48 µL) are mixed. Temperature is raised from 30° C. to 60° C. and the state of the mixture is observed at 30° C., 40° C., 50° C. and 60° C.

For each temperature, the mixture is monophasic (FIGS. 6a, 6b, 6c and 6d).

Example 2

Ionic liquid ($[C_{16}MIM][NTf_2]$, 0.672 g), triolein (0.202 g, 222 µL) and methanol (0.038 g, 48 µL) are mixed. Temperature is raised from 30° C. to 60° C. and the state of the mixture is observed at 30° C., 40° C., 50° C. and 60° C.

For each temperature, the mixture is monophasic (FIGS. 7a, 7b, 7c and 7d).

Example 3

Ionic liquid ($[C_{18}MIM][NTf_2]$, 0.295 g), triolein (0.541 g, 595 µL) and methanol (0.118 g, 150 µL) are mixed. Temperature is raised from 30° C. to 70° C. and the state of the mixture is observed at 30° C., 40° C., 50° C., 60° C. and 70° C.

At 30° C. the ionic liquid is solid, thus the mixture is biphasic solid/liquid. At 40° C., 50° C., 60° C. and 70° C., the ionic liquid is liquid and the mixture is monophasic (FIGS. 8a, 8b, 8c and 8d).

Example 4

Ionic liquid ($[C_{18}MIM][NTf_2]$, 0.448 g), triolein (0.404 g, 444 µL) and methanol (0.088 g, 112 µL) are mixed. Temperature is raised from 30° C. to 70° C. and the state of the mixture is observed at 30° C., 40° C., 50° C., 60° C. and 70° C.

At 30° C. and 40° C. the ionic liquid is solid, thus the mixture is biphasic solid/liquid. At 50° C., 60° C. and 70° C., the ionic liquid is liquid and the mixture is monophasic (FIGS. 8a, 8b, 8c and 8d).

Example 5

Ionic liquid ($[C_{18}MIM][NTf_2]$, 0.590 g), triolein (0.275 g, 302 µL) and methanol (0.060 g, 76 µL) are mixed. Temperature is raised from 30° C. to 70° C. and the state of the mixture is observed at 30° C., 40° C., 50° C., 60° C. and 70° C.

At 30° C. and 40° C. the ionic liquid is solid, thus the mixture is biphasic solid/liquid. At 50° C., 60° C. and 70° C., the ionic liquid is liquid and the mixture is monophasic (FIGS. 8a, 8b, 8c and 8d).

Example 6

Ionic liquid ($[C_{18}MIM][NTf_2]$, 0.672 g), triolein (0.202 g, 222 µL) and methanol (0.038 g, 48 µL) are mixed. Temperature is raised from 30° C. to 70° C. and the state of the mixture is observed at 30° C., 40° C., 50° C., 60° C. and 70° C.

At 30° C. and 40° C. the ionic liquid is solid, thus the mixture is biphasic solid/liquid. At 50° C., 60° C. and 70° C. the ionic liquid is liquid and the mixture is monophasic (FIGS. 8a, 8b, 8c and 8d).

Example 7

Ionic liquid ($[C_{18}MIM][PF_6]$, 0.448 g), triolein (0.404 g, 444 µL) and methanol (0.088 g, 112 µL) are mixed. Temperature is raised from 60° C. to 90° C. and the state of the mixture is observed at 60° C., 70° C., 80° C. and 90° C.

At 60° C. and 70° C. the ionic liquid is solid, thus the mixture is biphasic solid/liquid. At 80° C. and 90° C., the ionic liquid is liquid and the mixture is monophasic (FIGS. 9a, 9b, 9c and 9d).

2—Phase Behaviour

Example 8

Phase Behaviour of glycerol toward Different ionic liquids has been tested.

In all the experiments, 250 mg of ionic liquid and 600 mg of glycerol were mixed and strongly shaken for 2 minutes then incubated for 1 hour at 22° C. (room temperature).

Four different ionic liquids with $BF_4$ counter anion were tested: $[C_{12}MIM][BF_4]$, $[C_{14}MIM][BF_4]$, $[C_{16}MIM][BF_4]$, $[C_{18}MIM][BF_4]$.

In all the experimental conditions, two phases were observed. Glycerol and tested ionic liquids are non-miscible (FIG. 11).

Example 9

Phase behaviour of glycerol toward different ionic liquids has been tested.

In all the experiments, 250 mg of ionic liquid and 600 mg of glycerol were mixed and strongly shaken for 2 minutes then incubated for 1 hour at 22° C. (room temperature).

Four different ionic liquids with $PF_6$ counter anion were tested: $[C_{12}MIM][PF_6]$, $[C_{14}MIM][PF_6]$, $[C_{16}MIM][PF_6]$, $[C_{18}MIM][PF_6]$.

In all the experimental conditions, two phases were observed. Glycerol and tested ionic liquids are non-miscible (FIG. 12).

Example 10

Phase behaviour of glycerol toward different ionic liquids has been tested.

In all the experiments, 250 mg of ionic liquid and 600 mg of glycerol were mixed and strongly shaken for 2 minutes then incubated for 1 hour at 22° C. (room temperature).

Four different ionic liquids with $NTf_2$ counter anion were tested: $[C_{12}MIM][NTf_2]$, $[C_{14}MIM][NTf_2]$, $[C_{16}MIM][NTf_2]$, $[C_{18}MIM][NTf_2]$.

In all the experimental conditions, two phases were observed. Glycerol and tested ionic liquids are non-miscible (FIG. 13).

Example 11

Phase behaviour of methyl oleate toward different ionic liquids has been tested.

In all the experiments, 250 mg of ionic liquid and 600 mg of methyl oleate were mixed and strongly shaken for 2 minutes then incubated 1 hour at 30° C.

Four different ionic liquids with $BF_4$ counter anion were tested: $[C_{12}MIM][BF_4]$, $[C_{14}MIM][BF_4]$, $[C_{16}MIM][BF_4]$, $[C_{18}MIM][BF_4]$.

In all the experimental conditions, two phases were observed. Methyl oleate and tested ionic liquids are non-miscible (FIG. 14).

Example 12

Phase behaviour of methyl oleate toward different ionic liquids has been tested.

In all the experiments, 250 mg of ionic liquid and 600 mg of methyl oleate were mixed and strongly shaken for 2 minutes then incubated 1 hour at 30° C.

Four different ionic liquids with $PF_6$ counter anion were tested: $[C_{12}MIM][PF_6]$, $[C_{14}MIM][PF_6]$, $[C_{16}MIM][PF_6]$, $[C_{18}MIM][PF_6]$.

In all the experimental conditions, two phases were observed. Methyl oleate and tested ionic liquids are non-miscible (FIG. 15).

Example 13

Phase behaviour of methyl oleate toward different ionic liquids has been tested.

In all the experiments, 250 mg of ionic liquid and 600 mg of methyl oleate were mixed and strongly shaken for 2 minutes then incubated 1 hour at 30° C.

Three different ionic liquids with $NTf_2^-$ counter anion were tested: $[C_{14}MIM][NTf_2]$, $[C_{16}MIM][NTf_2]$, $[C_{18}MIM][NTf_2]$.

In all the experimental conditions, two phases were observed. Methyl oleate and tested ionic liquids are non-miscible (FIG. 16).

Example 14

Phase behaviour of the three member system methyl oleate, glycerol and $[C_{18}MIM][NTf_2]$ has been tested.

$[C_{18}MIM][NTf_2]$ (400 mg) was added to methyl oleate (800 mg) and glycerol (800 mg). The mixture was shaken for 2 minutes at room temperature (22° C.).

Three phases are formed:

Glycerol on the bottom (liquid inferior phase), $[C_{18}MIM][NTf_2]$ in the middle (solid phase), Methyl oleate on the top (liquid superior phase).

$[C_{18}MIM][NTf_2]$, methyl oleate and glycerol are not miscible at room temperature (FIG. 17).

Example 15

Phase behaviour of methyl oleate and glycerol toward different ionic liquids has been tested.

In all the experiments, 2.5 g of ionic liquid, 500 mg of methyl oleate and 500 mg of glycerol were mixed and strongly shaken for 2 minutes then incubated for 1 hour at 22° C. (room temperature).

Four different ionic liquids with $BF_4$— counter anion were tested: $[C_{12}MIM][BF_4]$, $[C_{14}MIM][BF_4]$, $[C_{16}MIM][BF_4]$, $[C_{18}MIM][BF_4]$.

For every ionic liquid tested, a three phases system was observed. Glycerol (bottom phase), tested ionic liquids (middle phase,) and methyl oleate (top phase) are non-miscible (FIG. 18).

Example 16

Phase behaviour of methyl oleate and glycerol toward different ionic liquids has been tested.

In all the experiments, 2.5 g of ionic liquid, 500 mg of methyl oleate and 500 mg of glycerol were mixed and strongly shaken for 2 minutes then incubated for 1 hour at 22° C. (room temperature).

Four different ionic liquids with $PF_6$— counter anion were tested: $[C_{12}MIM][PF_6]$, $[C_{14}MIM][PF_6]$, $[C_{16}MIM][PF_6]$, $[C_{18}MIM][PF_6]$.

For every ionic liquid tested, a three phases system was observed. Glycerol (bottom phase), tested ionic liquids (middle phase,) and methyl oleate (top phase) are non-miscible (FIG. 19).

Example 17

Phase behaviour of methyl oleate and glycerol toward different ionic liquids has been tested.

In all the experiments, 2.5 g of ionic liquid, 500 mg of methyl oleate and 500 mg of glycerol were mixed and strongly shaken for 2 minutes then incubated for 1 hour at 22° C. (room temperature).

Three different ionic liquids with $NTf_2^-$ counter anion were tested: $[C_{14}MIM][NTf_2]$, $[C_{16}MIM][NTf_2]$, $[C_{18}MIM][NTf_2]$.

For every ionic liquid tested, a three phases system was observed. Glycerol (bottom phase), tested ionic liquids (middle phase,) and methyl oleate (top phase) are non-miscible. $[C_{14}MIM][NTf_2]$ is liquid at room temperature (FIG. 20).

3—Comparative Experiments

Example 18

Ionic liquid ($[OMIM][NTf_2]$, 1.5 mL), refined soybean oil (1.5 mL) and methanol (preferred molar ration of methanol with respect to oil are 4:1 and 6:1) are stirred at 50° C. (Ha et al. 2007, *Enz. Microb. Technol.*).

The quantities of reagents as described by Ha et al. have been scaled down by 4, and the reaction mixture has been reproduced to investigate the state of the initial reactive phase when using an unrefined oil (triolein).

Ionic liquid $[OMIM][NTf_2]$ (0.375 mL), Triolein (0.375 mL) and methanol are mixed at different temperatures (40° C., 50° C. and 60° C.). Six different volumes of methanol were tested. Methanol molar ration with respect to oil are 2:1, 3:1, 4:1, 6:1, 8:1 and 10:1 (respectively 32 µL, 47 µL, 64 µL, 94 µL, 128 µL and 160 µL of methanol).

All the initial reaction mixtures obtained are biphasic (FIGS. 10a, 10b and 10c).

The reaction conditions described in the article by Ha et al. do not produce a monophasic initial reaction mixture.

III REACTION EXAMPLES

1. Biocatalytic Step 1.1 Reaction Medium

Example 19

Enzymatic synthesis of biodiesel in 1-methyl-3-octadecylimidazolium bis[(trifluoromethyl)sulfonyl]imide The transesterification reactions were carried out in 3-mL screw-capped vials with teflon-lined septa, containing 1.6 mL of 1-methyl-3-octadecylimidazolium bis[(trifluoromethyl)sulfonyl]imide, previously heated at 55° C., 0.18 mL (3.88 mmol) of methanol and 0.62 mL (0.64 mmol) of triolein. Then, the mixture was magnetically stirred at 50 rpm for 3 min at 60° C., resulting in a homogeneous solution. The synthesis of biodiesel started with the addition of 0.056 g of NOVOZYME 435 (NOVOZYMES, Novo Nordisk, Denmark), and the resulting reaction mixture was maintained at constant stirring (50 rpm) and temperature (60° C.) The reaction was monitored by HPLC (see Holapek, M. et al., 1999, Analytical monitoring of the production of biodiesel by high-performance liquid chromatography with various detection methods. J. Chromatogr. A, 858, 13-31). The biodiesel yields were 95.3% at 6 h and 99.0% after 24 h.

Example 20

Enzymatic Synthesis of Biodiesel in trioctylmethylammonium bis[(trifluoromethyl)sulfonyl]imide The transesterification reactions were carried out in 3-mL screw-capped vials with teflon-lined septa, containing 1.6 mL of trioctylmethylammonium bis[(trifluoromethyl)sulfonyl]imide, previously heated at 55° C., 0.24 mL (5.16 mmol) of methanol and 0.56 mL (0.58 mmol) of triolein. Then, the mixture was magnetically stirred at 50 rpm for 3 min at 60° C., resulting in a homogeneous solution. The synthesis of biodiesel started with the addition of 0.052 g of Novozym 435, and the resulting reaction mixture was maintained at constant stirring (50 rpm) at 60° C. The progress of the biodiesel synthesis was monitored by HPLC. The biodiesel yields were 80.0% after 6 h and 97.5% after 24 h.

Example 21

Enzymatic Synthesis of Biodiesel in $[C_{12}MIM][NTf_2]$, $[C_{14}MIM][NTf_2]$, $[C_{16}MIM][NTf_2]$, $[C_{18}MIM][NTf_2]$ Ionic Liquids Four experiments were performed, each with a different ionic liquid $[C_{12}MIM][NTf_2]$, $[C_{14}MIM][NTf_2]$, $[C_{16}MIM][NTf_2]$, or $[C_{18}MIM][NTf_2]$.

The selected ionic liquid (0.4 g), methanol (95 mg, 2.95 mmol), and triolein (437 mg, 0.49 mmol) are mixed in a 1.5 mL screw-capped test tube, incubated at 65° C. for 10 minutes and strongly shaken.

For each experiment, the reaction was started by adding lipase (lipase B) from *Candida antartica* (NOVOZYME 435, Novo-Nordisk Denmark), (150 mg). The reaction was shaken for 8 hours at 65° C.

The progress of the biodiesel synthesis was monitored by GC.

GC monitoring: Samples (15 µL) were taken from the tested solution and dissolved in $CH_2Cl_2$ (450 µL). 350 µL from the resulting solution were taken and added to an ethyl-decanoate solution in $CH_2Cl_2$ (150 µL, 100 mM) (Internal standard). Aliquots (1 µL) of the final solution are analysed by GC.

The biodiesel yields observed by GC, were 100.0% after 6 h for all the four ionic liquids tested.

Example 22

Enzymatic Synthesis of Biodiesel in $[C_{12}MIM][NTf_2]$, $[C_{14}MIM][NTf_2]$, $[C_{16}MIM][NTf_2]$, $[C_{18}MIM][NTf_2]$ Ionic Liquids Four experiments were performed, each with a different ionic liquid $[C_{12}MIM][NTf_2]$, $[C_{14}MIM][NTf_2]$, $[C_{16}MIM][NTf_2]$, or $[C_{18}MIM][NTf_2]$.

The selected ionic liquid (0.8 g), methanol (360 µL, 285 mg, 8.89 mmol), and triolein (1.44 mL, 1.31 g, 1.48 mmol) are mixed in a 3.5 mL screw-capped test tube, incubated at 65° C. for 10 minutes and strongly shaken.

For each experiment, the reaction was started by adding lipase (lipase B) from *Candida antartica* (Novosym® 435, Novo-Nordisk Denmark), (200 mg). The reaction was shaken for 8 hours at 65° C.

The progress of the biodiesel synthesis was monitored by GC.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in $CH_2Cl_2$ (150 µL, 100 mM) (Internal standard). Aliquots (1 µL) of the final solution are analysed by GC.

The biodiesel yields observed by GC, were as follow:
For $[C_{12}MIM][NTf_2]$, 59.4% after 2 hours, 70% after 6 hours, 70% after 8 hours.
For $[C_{14}MIM][NTf_2]$, 69.8% after 2 hours, 72.8% after 6 hours, 75.4% after 8 hours.
For $[C_{16}MIM][NTf_2]$, 68.61% after 2 hours, 72.8% after 6 hours, 81.05% after 8 hours.
For $[C_{18}MIM][NTf_2]$, 58.7% after 2 hours, 76% after 6 hours, 87% after 8 hours.

Example 23

Enzymatic Synthesis of Biodiesel in $[C_{12}MIM][PF_6]$, $[C_{14}MIM][PF_6]$, $[C_{16}MIM][PF_6]$, Ionic Liquids Three experiments were performed, each with a different ionic liquid $[C_{12}MIM][PF_6]$, $[C_{14}MIM][PF_6]$ or $[C_{16}MIM][PF_6]$.

The selected ionic liquid (0.8 g), methanol (360 µL, 285 mg, 8.89 mmol), and triolein (1.44 mL, 1.31 g, 1.48 mmol) are mixed in a 3.5 mL screw-capped test tube, incubated at 65° C. for 10 minutes and strongly shaken.

For each experiment, the reaction was started by adding lipase (lipase B) from *Candida antartica* (Novosym® 435, Novo-Nordisk Denmark), (200 mg). The reaction was shaken for 8 hours at 65° C.

The progress of the biodiesel synthesis was monitored by GC.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard). Aliquots (1 µL) of the final solution are analysed by GC.

The biodiesel yields observed by GC, were as follow:
For $[C_{12}MIM][PF_6]$, 30% after 6 hours.
For $[C_{14}MIM][PF_6]$, 38.6% after 6 hours.
For $[C_{16}MIM][PF_6]$, 49.4% after 6 hours.

Example 24

Enzymatic Synthesis of Biodiesel in $[C_{18}MIM][PF_6]$, Ionic Liquids

The ionic liquid ($[C_{18}MIM][PF_6]$, 0.8 g), methanol (720 µL, 570 mg, 17.77 mmol), and triolein (1.44 mL, 1.31 g, 1.48 mmol) are mixed in a 3.5 mL screw-capped test tube, incubated at 65° C. for 10 minutes and strongly shaken.

The reaction was started by adding lipase (lipase B) from *Candida antartica* (Novosym® 435, Novo-Nordisk Denmark), (200 mg). The reaction was shaken for 8 hours at 65° C.

The progress of the biodiesel synthesis was monitored by GC.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard). Aliquots (1 µL) of the final solution are analysed by GC.

Example 25

Enzymatic Synthesis of Biodiesel in $[C_{14}MIM][NTf_2]$, $[C_{16}MIM][NTf_2]$, $[C_{18}MIM][NTf_2]$ Ionic Liquids Three experiments were performed, each with a different ionic liquid $[C_{14}MIM][NTf_2]$, $[C_{16}MIM][NTf_2]$, or $[C_{18}MIM][NTf_2]$.

The selected ionic liquid (0.2 g), lipase (lipase B) from *Candida antartica* (Novosym® 435, Novo-Nordisk Denmark) (200 mg), and triolein (1.44 mL, 1.31 g, 1.48 mmol) are mixed in a 3.5 mL screw-capped test tube, incubated at 65° C. for 3 minutes and strongly shaken.

For each experiment, the reaction was started by adding methanol (360 µL, 285 mg, 8.89 mmol). The reaction was shaken for 24 hours at 65° C.

The progress of the biodiesel synthesis was monitored by GC after 2, 8 and 24 hours reaction time.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard).

The biodiesel yields observed by GC, were as follow:
For $[C_{14}MIM][NTf_2]$, 11% after 2 hours, 12.89% after 8 hours, 15.96% after 24 hours.
For $[C_{16}MIM][NTf_2]$, 15.9% after 2 hours, 17.1% after 8 hours, 18.9% after 24 hours.
For $[C_{18}MIM][NTf_2]$, 16.8% after 2 hours, 18.9% after 8 hours, 25.7% after 24 hours.

Example 26

Enzymatic Synthesis of Biodiesel in $[C_{14}MIM][PF_6]$, $[C_{16}MIM][PF_6]$, Ionic Liquids Two experiments were performed, one with $[C_{14}MIM][PF_6]$, the other with $[C_{16}MIM][PF_6]$.

The selected ionic liquid (0.2 g), lipase (lipase B) from *Candida antartica* (Novosym® 435, Novo-Nordisk Denmark) (200 mg), and triolein (1.44 mL, 1.31 g, 1.48 mmol) are mixed in a 3.5 mL screw-capped test tube, incubated at 65° C. for 3 minutes and strongly shaken.

For each experiment, the reaction was started by adding methanol (360 µL, 285 mg, 8.89 mmol). The reaction was shaken for 24 hours at 65° C.

The progress of the biodiesel synthesis was monitored by GC after 2, 8 and 24 hours reaction time.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard).

Example 27

Enzymatic Synthesis of Biodiesel in [$C_{14}$MIM][$BF_4$] or [$C_{16}$MIM][$BF_4$], Ionic Liquids Two experiments were performed, one in [$C_{14}$MIM][$BF_4$], the other in [$C_{16}$MIM][$BF_4$].

The selected ionic liquid (0.2 g), lipase (lipase B) from *Candida antartica* (Novosym® 435, Novo-Nordisk Denmark) (200 mg), and triolein (1.44 mL, 1.31 g, 1.48 mmol) are mixed in a 3.5 mL screw-capped test tube, incubated at 65° C. for 3 minutes and strongly shaken.

For each experiment, the reaction was started by adding methanol (360 µL, 285 mg, 8.89 mmol). The reaction was shaken for 24 hours at 65° C.

The progress of the biodiesel synthesis was monitored by GC after 2, 8 and 24 hours reaction time.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard).

The biodiesel yields observed by GC, were as follow:

For [$C_{14}$MIM][$BF_4$], 12.1% after 2 hours, 15.42% after 8 hours, 19.6% after 24 hours.

For [$C_{16}$MIM][$BF_4$], 9.1% after 2 hours, 16.0% after 8 hours, 24.15% after 24 hours.

Example 28

Enzymatic Synthesis of Biodiesel in [$C_{18}$MIM][FAP]

The ionic liquid ([$C_{18}$MIM][FAP], 0.2 g), lipase (lipase B) from *Candida antartica* (Novosym® 435, Novo-Nordisk Denmark) (200 mg), and triolein (1.44 mL, 1.31 g, 1.48 mmol) are mixed in a 3.5 mL screw-capped test tube, incubated at 65° C. for 3 minutes and strongly shaken.

For each experiment, the reaction was started by adding methanol (360 µL, 285 mg, 8.89 mmol). The reaction was shaken for 24 hours at 65° C.

The progress of the biodiesel synthesis was monitored by GC after 2, 8 and 24 hours reaction time.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard).

Example 29

Enzymatic Synthesis of Biodiesel in [$C_{18}$MIM][$NTf_2$]

The ionic liquid ([$C_{18}$MIM][$NTf_2$], 0.2 g), lipase (lipase B) from *Candida antartica* (Novosym® 435, Novo-Nordisk Denmark) (200 mg), and triolein (1.44 mL, 1.31 g, 1.48 mmol) are mixed in a 3.5 mL screw-capped test tube, incubated at 65° C. for 3 minutes and strongly shaken.

For each experiment, the reaction was started by adding ethanol (518 µL, 409 mg, 8.89 mmol). The reaction was shaken for 24 hours at 65° C.

The progress of the biodiesel synthesis was monitored by GC after 2, 8 and 24 hours reaction time.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard).

Example 30

Enzymatic Synthesis of Biodiesel in [$C_{18}$MIM][$NTf_2$]

The ionic liquid ([$C_{18}$MIM][$NTf_2$], 0.2 g), lipase (lipase B) from *Candida antartica* (Novosym® 435, Novo-Nordisk Denmark) (200 mg), and triolein (1.44 mL, 1.31 g, 1.48 mmol) are mixed in a 3.5 mL screw-capped test tube, incubated at 65° C. for 3 minutes and strongly shaken.

For each experiment, the reaction was started by adding 1-propanol (666 µL, 533 mg, 8.89 mmol). The reaction was shaken for 24 hours at 65° C.

The progress of the biodiesel synthesis was monitored by GC after 2, 8 and 24 hours reaction time.

GC monitoring: Samples (15 µL) were taken from the tested solution and dissolved in a solution of dodecane and 2-propanol (485 µL, dodecane:2-propanol volume ratio 95:5). The resulting biphasic mixtures are strongly shaken for 2 minutes and centrifuged at 12.000 rpm for 5 minutes. Then 350 µL from the top phase were taken and added to an ethyl-decanoate solution in dodecane (150 µL, 100 mM) (Internal standard).

1.2 Sample Analysis

Example 31

Reaction Medium

800 µL of 1-methyl-3-octadecylimidazolium bis[(trifluoromethyl)sulfonyl]imide (Ocdmim $NTf_2$)+90 µL Methanol from Merck (1.93 mmol)+310 µL Triolein (Technical grade, <60% GC triolein content, from Fluka) (0.32 mmol=0.96 mmol fatty acid chains)+28 mg NOVOZYME 435 (NOVOZYMES, Novo Nordisk, Denmark). Incubation was started in screw-capped glass vials into a glycerol bath at 60° C.

At different times, 30 µL samples were withdrawn from the reaction medium, then mixed with 470 mL of acetone into an Eppendorf vial. The resulting one phase mixture was centrifuged at 2,500 rpm for 15 min, to precipitate any enzyme particle. Then, 400 µL of clear solution were mixed with 100

μL of 100 mM ethyl decanoate (internal standard). Finally, 30 μL of the resulting solution were injected in a HPLC Shimadzu system, equipped with a LC20AD pump, SIL 20AC automatic injector and a SPD M20A diode array detector.

Samples were eluted through a LichroCart RP C-18 column (25 mm length, Merck), by using the following ternary gradient, and monitored at 210 nm wavelength.

| Time (min) | Phase A Acetonitrile:water (80:20 v/v) | Phase B Acetonitrile | Phase C Isopropanol:Hexane 50:40 v/v | Overall Flow (mL/min) |
|---|---|---|---|---|
| 0 | 100 | 0 | 0 | 1.2 |
| 5 | 0 | 100 | 0 | 1.2 |
| 7 | 0 | 100 | 0 | 1.2 |
| 20 | 0 | 50 | 50 | 1.2 |
| 28 | 0 | 100 | 0 | 1.2 |
| 30 | 0 | 100 | 0 | 1.2 |
| 33 | 100 | 0 | 0 | 1.2 |
| 35 | 100 | 0 | 0 | 1.2 |

Retention times of peaks were identified by using different commercial standards, as indicated in the following table

| Family | Compound | Retention time (min) |
|---|---|---|
| Fatty acids | Palmitic acid | 1.8 |
| | Oleic acid | 1.9 |
| Internal standard | Ethyl decanoate | 6.8 |
| Monoglycerides (MG) | Monopalmitin | 2.1 |
| | Monolinolein | 6.4 |
| | Monoolein | 8.2 |
| | Monostearin | 11.8 |
| FAMEs (Biodiesel) | Methyl palmitoleate | 9.1 |
| | Methyl linoleate | 9.6 |
| | Methyl oleate | 12.1 |
| | Methyl palmitate | 12.6 |
| | Methyl state | 15.0 |
| Diglycerides (DG) | 1,3-Dilinolein | 15.8 |
| | 1,2-Distearin | 16.4 |
| | 1,3-Diolein | 19.3 |
| | 1,3-Distearin | 19.5 |
| Triglycerides | Trilinolein | 23.5 |
| | Triolein | 27.8 |

It is necessary to take into account that not all the standards of TAG, DAG or MAG are available, that the substrate is not a pure compound, and that the chromatographic column is not able to separate all the compounds specifically. However, all the compounds of the same family e.g. TAG, DAG, MAG or FAME have a retention time in the same range in the chromatogram, and may be quantified together by their potential to transfer acyl groups. The presence of the IL into the injection sample (samples were dissolved in acetone) provokes a large elution peak from 1.5 to 4 min retention time, which makes impossible to quantify any compound in this time interval.

2. Biodiesel Recovery and IL Recycle Steps

Example 32

2.1. Enzyme Recovery

At the end of the reaction, the reaction mixture is centrifuged for 10 min at 2500 rpm and 40-50° C. (a temperature able to maintain liquid the reaction mixture), then the immobilized enzyme particles are recovered by simple decantation. The immobilized enzyme particles are stored in a desiccator containing silica gel at room temperature until the next catalytic cycle.

2.2. Elimination of Methanol

The reaction mixture is placed into a vessel, rotator flask or any other system able to permit vacuum (i.e. Buchi rotator system). The excess of methanol is removed by evaporation of the reaction mixture under reduced pressure at 50-70° C. (by using a bath water) and 100 rpm, for 10 min to 1 hour. The evaporation time depends on the overall volume of the reaction mixture.

2.3. Elimination of Glycerol

The removal of glycerol is carried out by liquid-liquid extraction with water. The added amount of water ranges from 2:1 to 5:1 v/v with respect to the full reaction volume, resulting in a biphasic system which is gently shaken at 25-100 rpm for 10 to 60 min at 30 to 90° C. After the shaking period, the reactor is introduced into an ice bath, for 3-5 min to decrease the temperature below 20° C., which may produce the solidification of the ionic liquid containing biodiesel. Then, the aqueous fraction is separated by simple decantation. This process could be repeated from 3 to 5-times.

2.4. Biodiesel Recovery

The extraction of biodiesel is carried out in the same reactor by liquid-liquid extraction with an organic solvent. Preferred organic solvents are non-miscible with the ionic liquids used in the process, usually short-chain aliphatic alkanes, such as pentane, hexane, heptane, octane, nonane, decane, and mixtures thereof. Toluene, mixture of xylenes, chlorobenzene can be used as well. The added amount of organic solvent ranges from 2:1 to 5:1 v/v with respect to the total reaction volume, resulting in an organic solvent-ionic liquid biphasic system which is maintained under gentle shaking or stirring (25-100 rpm) for a period of 10 to 60 min at a temperature of 30 to 90° C. After the shaking period, the organic solvent phase containing the biodiesel can be separated by simple decantation. This extraction process could be repeated from 3 to 5-times until the full extraction of biodiesel.

2.5. Drying of the IL

Once the selective extraction and separation of the excess of primary aliphatic alcohol, glycerol and biodiesel is achieved, the remaining IL and enzyme can be then used in further catalytic cycles.

Preferentially, the remaining enzyme-IL mixture left after the extraction of biodiesel is treated under vacuum for a period of 2 to 10 min at a temperature of 50 to 70° C. in order to remove all the residual organic solvent. The mixture enzyme-IL is then ready for a new biocatalytic cycle.

3. Example of a Full Catalytic Cycle and Recycling Process

Example 33

4 mL of 1-methyl-3-octadecylimidazolium bis[(trifluoromethyl)sulfonyl]imide, previously heated at 55° C., and 0.45 mL (9.68 mmol) of methanol were added into a 25-mL vacuum flask. The resulting solution was stirred at 100 rpm in the rotator system for 3 min at 60° C. Then, 1.55 mL (1.6 mmol) of triolein was added, and the mixture was again stirred at 100 rpm for 3 min at 60° C., turning into a homogeneous and clear solution. The synthesis of biodiesel started with the addition of 0.2 g NOVOZYME 435, and the resulting reaction mixture was maintained at constant stirring (150 rpm) for 24 h at 60° C. The progress for biodiesel synthesis was followed by HPLC. When the biocatalytic step was finished, three consecutive extractions were carried out to obtain products.

Firstly, the reaction mixture was put under vacuum for 5-10 min at 60° C. to remove the excess of methanol, which can be possibly reused in further catalytic cycles.

Secondly, 10 mL of water were added to the reaction mixture and the resulting biphasic mixture was stirred at 100 rpm for 30 min at 60° C. at atmospheric pressure. Then, the flask was introduced into an ice bath for 5 min to decrease the temperature below 20° C., which induced the solidification of the ionic liquid phase, the aqueous phase being the upper phase containing the glycerol. The aqueous fraction was collected by simple decantation. This step can be carried out two additional times to ensure complete extraction of glycerol if necessary.

Thirdly, 10 mL of hexane was added to the flask containing the solidified reaction mixture, and the mixture was stirred at 100 rpm and 60° C. for 30 min, resulting in a biphasic liquid mixture. Then, the hexane phase containing biodiesel was collected by simple decantation. This step can be carried out two additional times to ensure the full extraction of biodiesel.

After the last washing step with hexane, the remaining ionic liquid phase which contained the immobilized enzyme was put under vacuum pressure for 10 min at 60° C. to extract the remaining traces of hexane. Thus, the ionic liquid-enzyme mixture was ready to start a new cycle.

The obtained yields in biodiesel synthesis after consecutive operation cycles were as follows,

| CYCLE | Yield at 6 h (%) | Yield at 24 h (%) |
|---|---|---|
| 1 | 96.7 | 96.6 |
| 2 | 95.4 | 98.6 |
| 3 | 93.8 | 96.8 |
| 4 | 97.5 | 98.8 |
| 5 | 92.5 | 95.3 |
| 6 | 92.9 | 95.9 |
| 7 | 92.1 | 93.1 |

The invention claimed is:

1. A method for esterification and/or trangesterfication of a substrate with an alcohol, the method comprising:
   (1) combining the substrate with at least one alcohol, at least one ionic liquid and at least one enzyme, wherein:
      said substrate comprises oils, fats, fatty acids, or a mixture thereof,
      said ionic liquid, said substrate, and said alcohol form a single homogeneous liquid phase at the temperature at which the esterification and/or transesterification is performed, and
      said at least one ionic liquid is lipophilic, non miscible with water, and comprises a cation having a cationic head and an anion having an anionic head; and
   (2) carrying out the esterification and/or transesterification of the substrate,
      wherein, said cationic head and/or anionic head are independently substituted by one or more carbon side chains, which may be the same or different, the carbon side chains being linear or branched, saturated or unsaturated carbon chains, provided that at least one of the side chains comprises at least 10 carbon atoms.

2. The method according to claim 1, wherein three phases are formed at the end of the esterification and/or transesterification process,
   a first phase comprising the at least one ionic liquid and the at least one enzyme,
   a second phase comprising glycerol, and
   a third phase comprising fatty acid alkyl esters.

3. The method according to claim 1, wherein said ionic liquid is solid at room temperature.

4. The method according to claim 1, wherein said ionic liquid, said substrate, and said alcohol form a single homogeneous liquid phase at room temperature.

5. The method according to claim 1, wherein the enzyme is supported or non-supported, and said supported or non supported enzyme is suspended or dissolved within the single homogeneous liquid phase.

6. The method according to claim 1, wherein the ionic liquid has a melting temperature that is lower than the temperature of the esterification and/or transesterification process.

7. The method according to claim 1, wherein
   the ionic liquid cation is selected from imidazolium, pyridinium, triazolium, pyrrolidinium, guanidinium, sulfonium, phosphonium or ammonium cations, substituted by at least one lipophilic carbon side chain comprising at least 10 carbon atoms, and
   the ionic liquid anion is selected from $PF_6^-$, bis(trifluoromethylsulfonyl)imide ($NTf_2^-$) $BF_4^-$, tris(pentafluoroethyl)trifluorophosphate (FAP), alkylsulfates with an alkyl chain from 1 to 20 carbon atoms, alkylsulfonates with an alkyl chain from 1 to 20 carbon atoms, $Cl^-$, $I^-$, $Br^-$, or dialkylphosphate with alkyl chains from 1 to 20 carbon atoms.

8. The method according to claim 1, wherein the enzyme is at least one lipase obtained from *Candida antartica, Candida rugosa, Candida cylindracea, Pseudomonas cepacia, Mucor miehei, Mucor javaicus, Aspergillus niger*, swine pancreas, *Aspergillus subtilis, Bacilus subtilis, Aspergillus orayze, Rhvzopus oryzae, Chromobacterium visocosum, Yarrowia lipolitica, Thermus lanuginose* or pig liver.

9. The method according to claim 1, wherein the substrate comprises animal fats, sunflower seed oil, soybean oil, palm oil, coconut oil, linseed oil, rapeseed oil, corn oil, cottonseed oil, around nut oil, canola oil, olive oil, castor oil, jatropha oil, waste product oils, or mixtures thereof.

10. The method according to claim 1, wherein the at least one alcohol is an alcohol having from 1 to 4 carbon atoms or mixture thereof.

11. A process for the esterification and/or transesterification of a substrate comprising oils, fats, fatty acids, or a mixture thereof, into fatty acid alkyl esters, the process comprising the method according to claim 1, the process further comprising, after carrying out the esterification and/or transesterification of the substrate, one or more recovery step selected from:
   recovering the fatty acid alkyl esters formed in the esterification and/or transesterification reaction,
   recovering the glycerol formed in the esterification and/or transesterification reaction, and
   recovering the ionic liquid and the enzymes.

12. The process according to claim 11, wherein the substrate, alcohol, and ionic liquid form the single homogeneous liquid phase at room temperature, the process further comprising after carrying out the esterification and/or transesterification of the substrate:

recovering a phase comprising fatty acid alkyl esters formed in the esterification and/or transesterification reaction, recovering a phase comprising glycerol formed in the esterification and/or transesterification reaction, and recovering a phase comprising the ionic liquid and the enzyme, said ionic liquid being either liquid or solid, and purifying the ionic liquid and the enzyme from said recovered phase.

13. The process according to claim 12, further comprising reinitiating the process by bringing together the purified ionic liquid and enzymes with at least one substrate and at least one alcohol, forming a cycle.

14. The process according to claim 13, further comprising repeating at least one additional cycle of said process.

15. The process according to claim 14, wherein said cycles are repeated until the catalytic activity of the enzyme is exhausted, and further comprising removing the exhausted enzyme from the ionic liquid to give a regenerated ionic liquid.

16. The process according to claim 12, comprising:
combining the substrate, methanol, *Candida* lipase 1-methyl-3-octadecylimidazolium bis(trifluoromethylsulfonyl)imide and forming a single homogeneous liquid phase, stirring the combination at 60° C. for 24 hours, decanting the phase comprising the fatty acid alkyl esters formed in the esterification and/or transesterification reaction, decanting the phase comprising the glycerol formed in the esterification and/or transesterification reaction, and recovering and purifying under vacuum the 1-methyl-3-octadecylimidazolium bis(trifluoromethylsulfonyl) imide and *Candida* lipase.

17. The method according to claim 1, wherein said at least one side chain comprises at least 16 carbon atoms.

18. The method according to claim 1, wherein the ionic liquid anion is $NTf_2^-$, $PF_6^-$, or an alkylsulfate with an alkyl chain from 1 to 20 carbon atoms.

19. The method according to claim 1, wherein the ionic liquid is selected from the group consisting of 1-methyl-3-octadecylimidazolium bis(trifluoromethylsulfonyl)imide, 1-hexadecyl-3-methylimidazolium bis(trifluoromethylsulfonyl)imide and trimethyloctylammonium (bis(trifluoromethylsulfonyl)imide.

20. The method according to claim 11, wherein said at least one side chain comprises at least 16 carbon atoms.

* * * * *

UNITED STATES PATENT AND TRADEMARK OFFICE
CERTIFICATE OF CORRECTION

PATENT NO. : 8,470,565 B2  
APPLICATION NO. : 13/130463  
DATED : June 25, 2013  
INVENTOR(S) : Lozano et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 16 days.

Signed and Sealed this
Eighth Day of September, 2015

Michelle K. Lee
*Director of the United States Patent and Trademark Office*